(12) United States Patent
Santhanam et al.

(10) Patent No.: US 9,023,327 B2
(45) Date of Patent: May 5, 2015

(54) DICKKOPF-1 EXPRESSION MODULATING COMPOSITIONS AND USES THEREOF

(75) Inventors: Uma Santhanam, Tenafly, NJ (US); Qi Hong, Whippany, NJ (US); Sunghan Yim, Lincoln Park, NJ (US)

(73) Assignee: Avon Products, Inc., New York, NY (US)

(*) Notice: Subject to any disclaimer, the term of this patent is extended or adjusted under 35 U.S.C. 154(b) by 0 days.

(21) Appl. No.: 13/599,631

(22) Filed: Aug. 30, 2012

(65) Prior Publication Data

US 2014/0065086 A1  Mar. 6, 2014

(51) Int. Cl.
| | |
|---|---|
| *A61K 8/99* | (2006.01) |
| *A61Q 7/02* | (2006.01) |
| *A61Q 19/00* | (2006.01) |
| *A61Q 19/02* | (2006.01) |
| *A61P 29/00* | (2006.01) |
| *A61P 17/02* | (2006.01) |
| *A61Q 19/08* | (2006.01) |
| *A61P 25/00* | (2006.01) |
| *A61P 17/10* | (2006.01) |
| *A61K 36/06* | (2006.01) |
| *A61P 17/00* | (2006.01) |
| *A61K 36/896* | (2006.01) |

(52) U.S. Cl.
CPC ... *A61K 8/99* (2013.01); *A61Q 7/02* (2013.01); *A61Q 19/02* (2013.01); *A61Q 19/08* (2013.01); *A61K 36/06* (2013.01); *A61K 36/896* (2013.01); *A61K 2236/19* (2013.01)

(58) Field of Classification Search
None
See application file for complete search history.

(56) References Cited

U.S. PATENT DOCUMENTS

| | | | |
|---|---|---|---|
| 2,239,345 A | 4/1941 | Sperti | |
| 5,643,587 A | 7/1997 | Scancarella et al. | |
| 5,676,956 A | 10/1997 | Duffy et al. | |
| 5,776,441 A | 7/1998 | Scancarella et al. | |
| 5,980,904 A * | 11/1999 | Leverett et al. | 424/725 |
| 6,461,857 B1 | 10/2002 | Scholz et al. | |
| 6,562,321 B2 * | 5/2003 | Ptchelintsev et al. | 424/62 |
| 6,858,212 B2 | 2/2005 | Scholz et al. | |
| 8,198,244 B2 | 6/2012 | Hearing et al. | |
| 2003/0129259 A1 * | 7/2003 | Mahalingam et al. | 424/727 |
| 2003/0198682 A1 | 10/2003 | Gruber et al. | |
| 2004/0043084 A1 * | 3/2004 | Cioca et al. | 424/725 |
| 2004/0067245 A1 | 4/2004 | Mahalingam et al. | |
| 2004/0126344 A1 | 7/2004 | Mahalingam et al. | |
| 2005/0032751 A1 * | 2/2005 | Wang et al. | 514/114 |
| 2005/0287089 A1 | 12/2005 | Mahalingam et al. | |
| 2006/0110815 A1 * | 5/2006 | Gruber | 435/254.2 |
| 2008/0234139 A1 * | 9/2008 | Shaughnessy et al. | 506/9 |
| 2010/0021532 A1 * | 1/2010 | Rao et al. | 424/450 |
| 2010/0135941 A1 * | 6/2010 | Watanabe et al. | 424/62 |

FOREIGN PATENT DOCUMENTS

| | | |
|---|---|---|
| JP | 2003292416 A | 10/2003 |
| JP | 2003306424 A | 10/2003 |
| WO | WO 2009067095 A1 * | 5/2009 |

OTHER PUBLICATIONS

Y. Yamaguchi et al., Mesenchymal-epithelial interactions in the skin: increased expression of dickkopf1 by palmoplantar fibroblasts inhibits melanocyte growth an differentiation, The Journal of Cell Biology, Apr. 26, 2004; 165(2): 275-285.

Y. Yamaguchi et al., The Effects of Dickkopf 1 on Gene Expression and Wnt Signaling by Melanocytes: Mechanisms Underlying Its Suppression of Melanocyte Function and Proliferation, The Society for Investigative Dermatology, May 2007; 127(5): 1217-25.

Y. Yamaguchi et al., Dickkopf 1 (DKK1) regulates skin pigmentation and thickness by affecting Wnt/B-catenin signaling in keratinocytes, The FASEB Journal Apr. 2008; 22(4): 1009-20.

Y. Yamauchi et al., Regulation of Skin Pigmentation and Thickness by Dickkopf 1 (DKK1), Journal of Investigative Dermatology Symposium Proceedings Aug. 2009; 14(1): 73-75.

* cited by examiner

*Primary Examiner* — Rachael E Bredefeld
*Assistant Examiner* — Dominic Lazaro
(74) *Attorney, Agent, or Firm* — David M. Joyal; Joan M. McGillycuddy

(57) ABSTRACT

The present invention relates generally to compositions for topical application to the skin which comprise at least one DICKKOPF-1 expression modulator and the use of such compositions to provide benefits to the skin, including but not limited to lightening or darkening skin; treating hyper or hypopigmented skin; increasing or decreasing skin thickness; reducing or increasing skin hirsuteness; and/or changing skin phenotype from non-palmoplantar to palmoplantar.

10 Claims, 2 Drawing Sheets

Untreated     Essence Formula

DICKKOPF-1 EXPRESSION MODULATING COMPOSITIONS AND USES THEREOF

FIELD OF THE INVENTION

The present invention relates generally to compositions for topical application to the skin which comprise at least one DICKKOPF-1 expression modulator and the use of such compositions to provide benefits to the skin, including but not limited to lightening skin; treating hyperpigmented skin; increasing skin thickness; decreasing pigmentation; reducing skin hirsuteness; and/or changing skin phenotype from non-palmoplantar to palmoplantar.

BACKGROUND OF THE INVENTION

There is an increasing demand in the cosmetics industry to develop products that may be applied topically to the skin that improve the condition and appearance of skin. Consumers are interested in mitigating or delaying the dermatological signs of chronologically- or hormonally-aged skin, as well as skin aging due to environmental stress, such as fine lines, wrinkles, sagging skin and other conditions due to a progressive loss of cell growth, proliferation and functionality in the epidermal and dermal skin layers. During the aging process, the complexion of the skin, i.e., the color and appearance of the skin, deteriorates slowly from aging and/or prolonged exposure to environmental stress, e.g., sunlight. Numerous cosmetic and medical treatments have been developed in an attempt to treat environmentally damaged, aging or aged skin. However, such cosmetics or treatments commonly contain organic acids as their active ingredients or components, and are frequently associated with consumer discomfort, such as burning, itching, and redness.

Numerous means for obtaining a white or pale complexion are known and include skin lightening creams, bleaches, peels, and oral and injectable medication. Many of the known active ingredients include alpha hydroxy acids, kojic acid, ascorbic acid, hydroquinone, and glutathione, in addition to natural extracts, licorice, *Glycyrrhiza glabra*, arbutin, bearberry, *Chlorella vulgaris* extract, *Perilla* extract, and coconut fruit extract, as well as derivatives of any of the previously mentioned active ingredients. These and other known lightening products work in various ways. Some are based on inhibiting the production of melanin, which is responsible for pigmentation, eg. thiodipropionic acid, such as described in US Patent Application Publication Serial No. 2004/0126344, herein incorporated in its entirety for all purposes. Others are acids that remove old skin by promoting exfoliation, for example, alpha hydroxyl acids. Although many of these lightening agents do work, many may have serious side effects.

Some of the side effects of lightening agents include, but are not limited to: redness, itching, stinging, burning, crusting, swelling, unusual discoloration, and more serious side effects such as ochronosis, i.e., the appearance of very dark patches of skin that are difficult to remove. Leukoderma, where the skin loses the ability to produce pigment altogether, resulting in patches of pink, may also result from using some known lighteners.

DICKKOPF-1, which is a protein that is highly expressed in dermal fibroblasts of human skin on the palms and soles, has been shown to have a paracrine action on melanocytes, inhibiting the function and proliferation of melanocytes in epidermis; this is believed to be one of the mechanisms controlling pigmentation on palmo-plantar skin. (*J. Cell Biol.* 2004 Apr. 26; 165(2):275-85, *J Invest Dermatol.* 2007 May; 127(5):1217-25. *FASEB J.* 2008 April; 22(4):1009-20, *J Investig Dermatol Symp Proc.* 2009 August; 14(1):73-5). U.S. Pat. No. 8,198,244 describes topically administering DICKKOPF-1 to increase skin thickness, decrease skin pigmentation, and/or reduce hair growth.

*Clintonia borealis* (*C. borealis*), more commonly referred to as the Bluebeard Lily, is found in the eastern to central North American regions. This perennial plant grows up to 12 inches in height, with leathery, shiny leaves, blue berries and yellow bell-like flowers on a tall leafless stalk that is in full bloom from May-July. Native American Indians, such as the Potawatami and Algonquins, used *Clintonia* for a number of medicinal purposes. For example, fresh poulticed leaves were applied topically to burns, sores, bruises and rabid animal bites for the plant's anti-inflammatory properties. The root of the plant was used to ease childbirth, and Arch Chemicals has subsequently prepared an extract from the roots of *C. borealis* marketed as NAB® *Clintonia Borealis*. JP 2003306424 describes cosmetics containing *Uvularia* extracts (including *C. borealis*) for enhancing activities of skin-lightening agents. JP 2003292416 A describes a skin external agent containing extractive solution of plant of *C. borealis* with effects in moistening skin and preventing pachylosis and pigmentation, and includes a working example of an ethanolic extraction of *C. borealis*.

Many of the physiological processes in play in the development of undesirable skin or hair have counterparts in eukaryotic microorganisms, such as yeast, and yeast extracts have been used in cosmetic applications. For example, in response to heat, UV radiation, or other stress, yeast are known to produce factors that promote cell proliferation or viability. See, e.g., U.S. Pat. No. 2,239,345. Stressed yeast lysates containing such factors have been described and have been indicated for use in cosmetic applications directed to counteracting the effects of certain stresses on the skin. For example, UV-stressed yeast lysates have been used in cosmetic applications. See, e.g., U.S. Pat. Nos. 5,643,587; 5,676, 956; and 5,776,441. More recently, ozone-stressed yeast lysates have been described as useful in protecting skin cells from the harmful effects of ozone. See, e.g., U.S. Pat. Nos. 6,461,857 and 6,858,212 to Scholz et al; and U.S. Pat. Appl. Pub. Nos. 2003/0198682 and 2006/0110815. U.S. Pat. Appl. Pub. No. 2010/0021532 describes a yeast/polyphenol ferment extract that contains new actives beneficial to the skin, wherein the new actives result from a yeast belonging to the genus of *Pichia* being exposed to a non-cytotoxic amount of a polyphenol as a growth factor during a key stage of fermentation. Nonetheless, these earlier cases failed to recognize certain cosmetic uses and failed to identify active ingredients within the cellular lysates.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

BRIEF SUMMARY OF THE INVENTION

In accordance with the foregoing objectives and others, it has surprisingly been found that yeast extract prepared by fermenting *C. borealis* extract with yeast for a time sufficient for the yeast to metabolize the *C. borealis* extract, lysing the yeast, and then purifying soluble yeast lysate components so as to eliminate water-insoluble components can be utilized to increase DICKKOPF-1 expression and thus can be utilized in compositions and methods of treatment to provide benefits to the skin, including but not limited to lightening skin; treating hyperpigmented skin; decreasing pigmentation; increasing skin thickness; reducing skin hirsuteness; and/or changing skin phenotype from non-palmoplantar to palmoplantar phenotype driving effects.

Generally, the compositions and methods are useful for treating any skin condition associated with hyperpigmentation; thin skin; hirsute skin; and/or undesirably dark skin tone. These benefits are believed to arise, at least in part, from the ability of the compounds to increase cellular expression of the DICKKOPF-1 protein. In other words, the compounds of the invention are DICKKOPF-1 expression enhancers.

Another aspect of the invention relates to cosmetic use of compositions containing yeast isolates resulting from yeast metabolization of *C. borealis* extract to provide at least one benefit to human skin. Such benefits include:

(a) treatment and/or prevention of fine lines or wrinkles;
(b) reduction of skin pore size;
(c) improvement in increasing and/or maintaining skin thickness, plumpness, and/or tautness, including treating and/or preventing thinning skin;
(d) improvement in skin suppleness and/or softness;
(e) improvement in skin tone, radiance, and/or clarity;
(f) improvement in skin texture and/or promotion of retexturization;
(g) improvement in skin barrier repair and/or function;
(h) improvement in appearance of skin contours;
(i) restoration of skin luster and/or brightness;
(j) replenishment of essential nutrients and/or constituents in the skin;
(k) improvement of skin appearance decreased by menopause;
(l) improvement in skin moisturization and/or hydration;
(m) increase in and/or preventing loss of skin elasticity and/or resiliency;
(n) improvement in procollagen and/or collagen synthesis;
(o) treatment and/or prevention of skin sagging or atrophy;
(p) enhancing exfoliation and/or reducing dryness;
(q) treatment and/or prevention of skin hyper-pigmentation;
(r) treatment of and/or prevention of acne marks and/or post-inflammatory hyperpigmentation.
(s) treatment and/or prevention of excess sebum output;
(t) treatment and/or prevention of cellulite;
(u) decreasing pigmentation;
(v) lightening skin;
(w) treating hyperpigmented skin;
(y) changing skin phenotype from non-palmoplantar to palmoplantar phenotype.

The improvement in the unwanted feature and/or overall aesthetic appearance can include one or more of the following: lightening skin; treating hyperpigmented skin including spots, age spots, liver spots, uneven skin tone, post-acne marks, brown patches, blotchy red patches, freckles and sallowness; reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, reducing skin fragility; preventing skin atrophy; improving skin tone, radiance, and/or clarity; preventing, reducing, and/or ameliorating skin sagging; improving skin firmness, plumpness, tautness, suppleness and/or softness; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause, such as essential nutrients or other skin constituents; ameliorating the effects of estrogen imbalance; improving communication among skin cells; increasing cell proliferation and/or multiplication; increasing skin cell metabolism decreased by aging and/or menopause; retarding cellular aging; improving skin moisturization and/or hydration; increasing skin elasticity and/or resiliency; improving procollagen and/or collagen synthesis; enhancing exfoliation; improving microcirculation; reducing dryness; decreasing pigmentation; increasing skin thickness; reducing skin hirsuteness; and/or changing skin phenotype from non-palmoplantar to palmoplantar phenotype; and any combinations thereof.

In one embodiment, a method for improving the aesthetic appearance of human skin comprises topically applying to an area of hyper-pigmented skin a composition comprising an effective amount of a DICKKOPF-1 expression increasing agent in a cosmetically acceptable vehicle, wherein said DICKKOPF-1 expression increasing agent is present in an amount sufficient to decrease hyper-pigmentation in said area of hyper-pigmented skin.

In another embodiment, the DICKKOPF-1 expression increasing agent is a yeast/*C. borealis* ferment extract.

In another embodiment, the DICKKOPF-1 expression increasing agent excludes unmetabolized *C. borealis* extract.

In another embodiment, the DICKKOPF-1 expression increasing agent is present in the composition at between about __0.0001%-__10%__

In another embodiment, the DICKKOPF-1 expression increasing agent comprises a yeast/*C. borealis* ferment extract exhibiting a pH of between about 5.0 to about 7.0 when added to the composition.

In another embodiment, the DICKKOPF-1 expression increasing agent is derived from an aqueous *C. borealis* extract.

In another embodiment, the yeast is *Pichia. pastoris*.

In another embodiment, the DICKKOPF-1 expression increasing agent is in combination with at least one other skin lightener, selected from thiodipropionic acid (TDPA) or an ester derivative thereof.

In another embodiment, a method for improving the aesthetic appearance of human skin comprises topically applying to skin or hair to be lightened a composition comprising an effective amount of a DICKKOPF-1 expression increasing agent in a cosmetically acceptable vehicle for a time sufficient to lighten the skin or hair to be lightened.

In another embodiment, the method for providing a benefit to human skin comprises topically applying to skin in need thereof a composition comprising an effective amount of a DICKKOPF-1 expression increasing agent in a cosmetically acceptable vehicle.

In another embodiment, the said DICKKOPF-1 expression increasing agent is applied to skin exhibiting a non-palmoplantar phenotype.

In another embodiment, the benefit is increased skin thickness.

In another embodiment, the benefit is decreased hirsuitism.

In another embodiment, the effective amount of DICKKOPF-1 expression increasing agent is present in an amount sufficient to treat at least one dermatological pathology selected from the group consisting of a skin graft, a skin ulcer, a skin abrasion or avulsion/excision (such as one that leaves a volume defect), an injury or predisposition to injury caused by a repetitive impact or mechanical stress, age-related skin changes (for example photo-aged skin or thin skin), skin damage due to steroid treatment, uneven skin pigmentation, hyperpigmentation, post-inflammatory pigmentation, ephelides, fragrance dermatitis, vitiligo (for instance, where depigmentation is desired in a subject with widespread vitiligo), a pigmented birthmark (for example a cafe au lait spot), lentigos, or skin changes due to lichen simplex chronicus, melasma, porphyria cutanea tarda, Addison's disease, Peutz-Jeghers syndrome, acanthosis nigricans, hirsutism, congenital adrenal hyperplasia, polycystic ovarian syndrome, hypertrichosis, and anorexia nervosa.

In another embodiment, the skin benefit is selected from the group consisting of: (a) treatment of prevention of a sign of skin aging (b) treatment and/or prevention of fine lines or wrinkles; (c) reduction of skin pore size; (d) improvement in skin thickness, plumpness, and/or tautness; (e) improvement in skin suppleness and/or softness; (f) improvement in skin tone, radiance, and/or clarity; (g) improvement in skin texture and/or promotion of retexturization; (h) improvement in skin barrier repair and/or function; (i) improvement in appearance of skin contours; (j) restoration of skin luster and/or brightness; (k) replenishment of essential nutrients and/or constituents in the skin; (l) improvement of skin appearance decreased by menopause; (m) improvement in skin moisturization and/or hydration; (n) increase in and/or preventing loss of skin elasticity and/or resiliency; (O) improvement in procollagen and/or collagen synthesis; (p) treatment and/or prevention of skin sagging or atrophy; (q) enhancing exfoliation and/or reducing dryness; (r) treatment and/or prevention of skin hyper-pigmentation; (s) improvement in skin lightening; (t) treatment and/or prevention of excess sebum output; and (u) treatment and/or prevention of cellulite.

In another embodiment, the skin hyper-pigmentation comprises an age spot, a mottled area, a discrete hyper-pigmented area, a tanned area, an under-arm area, or a melasmic patch.

In another embodiment, the benefit comprises reducing inflammation comprised of an acne lesion, a pimple, or an irritated area.

In another embodiment, a topical composition comprises: from 0.001 weight % to 5 weight % of a DICKKOPF-1 expression increasing agent in a cosmetically acceptable vehicle; wherein said topical composition is in the form of a lotion, cream, essence ointment, gel, or stick.

In another embodiment, a method of treating the skin comprises topically applying to an area of the skin in need thereof an effective amount of an yeast fermentation product that modulates DICKKOPF-1 expression, wherein the ability of the yeast fermentation product to modulate DICKKOPF-1 expression has been determined by an assay which measures the level of mRNA encoding DICKKOPF-1 in a cell that has been contacted with the yeast fermentation product.

DETAILED DESCRIPTION OF THE INVENTION

Figure 1:
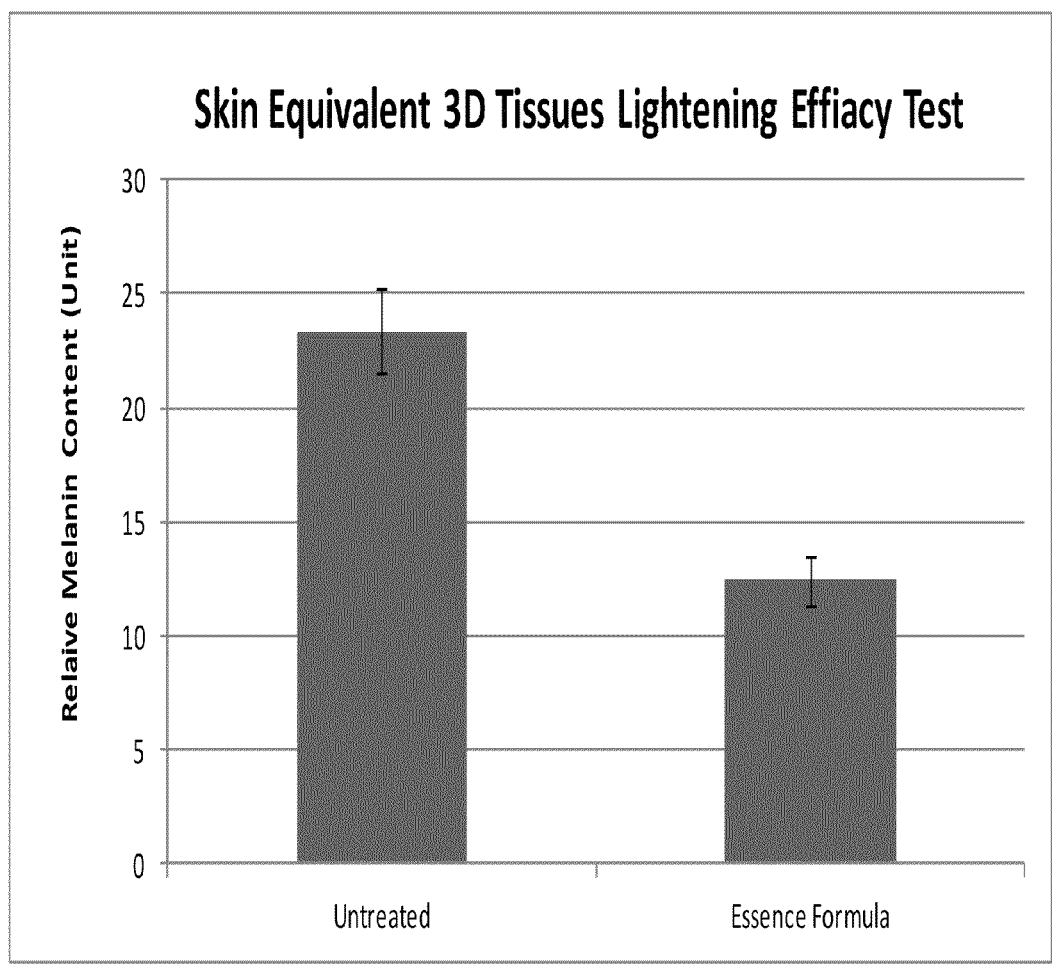
FIG. 1: Melanoderm™ 3D skin equivalent tissues where treated with a formulation of the instant invention or left untreated. After 14 days, melanin content was quantified and depicted graphically.

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, and some features may be exaggerated to show details of one embodiment components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

As used herein, "% by weight" or "% wt." refers to the weight percent of a component in relation to the total weight of the composition (i.e., including any carriers, vehicles, solvents, fillers, or other components added before application to the skin) unless otherwise provided.

Whenever a term is identified by reference to a range, the range will be understood to explicitly disclose every element thereof. As a non-limiting example, a range of 1-10% will be understood to include 1%, 2%, 3%, 4%, 5%, 6%, 7%, 8%, 9%, and 10% and all values between 1 and 10%.

Where two or more substituents are referred to as being "independently selected from" a group of enumerated alternatives, it is meant that each substituent can be any element of that group, independent of the identity of the other substituents.

As used herein, all terms are intended to have their ordinary meaning in the art unless specifically defined. For the purposes of describing and claiming the present invention, the following terms are defined:

The term "cosmetically acceptable vehicle" means: any vehicle known in the art suitable for application to skin and may include, but are not limited to, water; vegetable oils; mineral oils; esters such as octyl palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone; hydrocarbon oils such as mineral oil, petrolatum, isoeicosane and polyisobutene; polyols such as propylene glycol, glycerin, butylene glycol, pentylene glycol and hexylene glycol; liposomes; waxes; or any combinations or mixtures of the foregoing.

The term "decreased hirsuitism" means: A decrease in the amount of hair growth on a subject, measurable utilizing the Ferriman-Gawley score (Ferriman D M, Gallwey J D. Clinical assessment of body hair growth in women. J Clin Endocrinol 1961:21:1440-1447). It is a representation of hair growth in a male pattern on a woman shown in four different degrees of severity in 11 different body parts; namely the upper lip, chin, chest, upper back, lower back, upper abdomen, lower abdomen, arm, forearm, thigh, and lower leg. The Ferriman-Gawley scoring system is used to score the degree of excess male pattern body hair by doctors. The scorecard of every body location under survey begins from 0 (no excessive terminal hair growth) to 4 (extensive terminal hair growth)

and the numbers are added up to a maximum count of 36. While most experts refer to a modified score of 8 or more to diagnose hirsutism, some suggest a final tally of 6 or more is enough to indicate hirsutism. Based on this score pattern and other clinical tests, hirsutism can be evaluated as mild, moderate or severe.

The term "DICKKOPF-1" means: a peptide, in one embodiment a secreted antagonist of canonical Wnt signaling that interacts with Wnt receptor lipoprotein receptor-related protein 6 (LRP6) and with the transmembrane proteins Kremen (Krn) 1 and 2. DICKKOPF-1 blocks canonical Wnt signaling by inducing endocytosis of the LRP6 complex without affecting the Wnt receptor Frizzled. DICKKOPF-1 induces the formation of ectopic heads in *Xenopus laevis* in the presence of BMP inhibitors, and plays critical roles in modulating apoptosis during vertebrate limb development (especially inter-digit space formation) by interacting with BMP. As used herein, the term DICKKOPF-1 includes both human and non-human DICKKOPF-1 proteins (for example, rat, mouse, and chicken DICKKOPF-1), as well as functional DICKKOPF-1 fragments. Specific, nonlimiting examples of DICKKOPF-1 protein sequences are listed as GenBank Accession Nos. gi37183128, gi31542557, gi7110719, gi13124053, gi4545252, gi10281590, gi118092551, gi62858825, gi115313025, gi13124044, gi114630593, gi114630591, gi114630589, gi29504796, gi16306720, gi46394862, and gi5360731. Specific, non-limiting examples of DICKKOPF-1 fragments can be found in U.S. Pat. No. 7,057,017. One of ordinary skill in the art will recognize that these DICKKOPF-1 full-length proteins and DICKKOPF-1 fragments are provided merely as examples; other proteins that fall into the described class will be recognized.

The term "decreasing melanin synthesis" and related expressions refer to reducing the amount of one or more of the different types of melanin biosynthesized in skin and/or deposited in hair, and in one embodiment refers to reducing melanocyte-mediated hyper-pigmentation.

The term "is derived from an aqueous *C. borealis* extract" means: a composition resulting from a yeast fermentation process using *C. borealis* extract that is exclusively created using an aqueous extraction process.

The term "treating hyper-pigmentation" means: eradicating, reducing. ameliorating, or reversing a degree of subject pigmentation that results from increased presence of one or more of the different types of melanin biosynthesized in skin and/or follicles and deposited in hair or skin, relative to a subject's baseline pigmentation.

The term "lightening skin" means eradicating, reducing, ameliorating, and/or reversing a baseline degree of subject pigmentation. Lightening skin may be measured by observing changes in Fitzpatrick scale value of a subject. The Fitzpatrick Scale (aka Fitzpatrick skin typing test or Fitzpatrick phototyping scale) is a numerical classification schema for the color of skin, and remains a recognized tool for dermatologic research into the color of skin. The Fitzpatrick Scale measures several components, including Genetic Disposition, Reaction to Sun Exposure and Tanning Habits.
Type I (scores 0-7) White; very fair; freckles; typical albino skin.
Always burns, never tans
Type II (scores 8-16) White; fair.
Usually burns, tans with difficulty
Type III (scores 17-24) Beige; very common.
Sometimes mild burn, gradually tans to a light brown
Type IV (scores 25-30) Beige with a brown tint; typical Mediterranean Caucasian skin.
Rarely burns, tans with ease to a moderate brown.
Type V (scores over 30) Dark brown.
Very rarely burns, tans very easily
Type VI Black.
Never burns, tans very easily, deeply pigmented.

The term "yeast/*C. borealis* fermentation extract" means: a combination of cytolasmic and extracellular components of fermented yeast, that has been fermented with *C. borealis* extract, including but not limited to nutrient broth, cellular protein material, cellular nucleic material, cellular protoplasmic material and/or cell wall components.

All references to median or mean particle sizes herein are on a volume basis. All amounts provided in terms of weight percentage are relative to the entire composition unless otherwise stated.

One embodiment of the present disclosure relates to the novel use of yeast extracts, or more specifically, yeast/*C. borealis* fermentation extracts, or even more specifically, yeast/aqueous *C. borealis* extract fermentation extracts, in a topical composition for application on the face and/or body in order to improve the condition and aesthetic appearance of skin. In another embodiment the inventive yeast/*C. borealis* fermentation extract is provided in combination with one or more other active agents as hereinafter described.

It is to be understood that, as used herein, the terms treating and treatment include and encompass reducing, ameliorating, improving, alleviating, and/or eliminating the dermatological effects of aging and/or environmental stress. The present compositions and methods are suitable for use in treating dermatological conditions of the skin in numerous areas of the body, including, without limitation, the face, forehead, lips, neck, arms, hands, legs, knees, feet, chest, back, groin, buttocks, thighs, and the like. In an embodiment, the compositions are applied to the face.

In another embodiment, as used herein, the terms treating and treatment include and encompass skin lightening. The present compositions and methods are suitable for use in treating dermatological conditions of the skin in numerous areas of the body, including, without limitation, the face, forehead, lips, neck, arms, hands, legs, knees, feet, chest, back, groin, buttocks, thighs, and the like. In another embodiment, the compositions are applied to the face.

In another embodiment, as used herein, the terms treating and treatment include and encompass change of non-palmoplantar phenotype skin to palmoplantar phenotype skin. The present compositions and methods are suitable for use in treating dermatological conditions of the skin in numerous areas of the body, including, without limitation, the face, forehead, lips, neck, arms, hands, legs, knees, feet, chest, back, groin, buttocks, thighs, and the like. In an embodiment, the compositions are applied to the face.

In another embodiment, as used herein, the terms treating and treatment include and encompass decrease of hirsuteness. The present compositions and methods are suitable for use in treating dermatological conditions of the skin in numerous areas of the body, including, without limitation, the face, forehead, lips, neck, arms, hands, legs, knees, feet, chest, back, groin, buttocks, thighs, and the like. In another embodiment, the compositions are applied to the face.

In another embodiment, as used herein, the terms treating and treatment include and encompass thickening of skin and/or treatment of thin skin. The present compositions and methods are suitable for use in treating dermatological conditions of the skin in numerous areas of the body, including, without limitation, the face (especially the region between the nose and upper lip), forehead, lips, neck, arms, hands, legs, knees, feet, chest, back, groin, buttocks, thighs, and the like. In another embodiment, the compositions are applied to the face.

In accordance with the foregoing objectives and others, compositions that decrease DICKKOPF-1 expression can be utilized in compositions and methods of treatment to provide benefits to the skin, including but not limited to darkening skin; treating hyper or hypopigmented skin; increasing pigmentation; decreasing skin thickness; increasing hair growth; and/or changing skin phenotype from palmoplantar to non-palmoplantar phenotype driving effects.

Generally, the compositions and methods are useful for treating any skin condition associated with hyper or hypopigmentation; thick skin; scalp skin; and/or undesirably light skin tone. These benefits are believed to arise, at least in part, from the ability of the compounds to decrease cellular expression of the DICKKOPF-1 protein. In other words, the compounds of the invention are DICKKOPF-1 expression inhibitors.

In another embodiment, as used herein, the terms treating and treatment include and encompass skin darkening. The present compositions and methods are suitable for use in treating dermatological conditions of the skin in numerous areas of the body, including, without limitation, the face, forehead, lips, neck, arms, hands, legs, knees, feet, chest, back, groin, buttocks, thighs, and the like. In another embodiment, the compositions are applied to the face.

In another embodiment, as used herein, the terms treating and treatment include and encompass change of palmoplantar phenotype skin to non-palmoplantar phenotype skin. The present compositions and methods are suitable for use in treating dermatological conditions of the skin in numerous areas of the body, including, without limitation, the face, forehead, lips, neck, arms, hands, legs, knees, feet, chest, back, groin, buttocks, thighs, and the like. In an embodiment, the compositions are applied to the face.

In another embodiment, as used herein, the terms treating and treatment include and encompass increase of hair growth. The present compositions and methods are suitable for use in treating dermatological conditions of the skin in numerous areas of the body, including, without limitation, the face, scalp, eye brows, eye lashes, forehead, lips, neck, arms, hands, legs, knees, feet, chest, back, groin, buttocks, thighs, and the like. In another embodiment, the compositions are applied to the face.

In another embodiment, as used herein, the terms treating and treatment include and encompass thinning of skin and/or treatment of thick skin. The present compositions and methods are suitable for use in treating dermatological conditions of the skin in numerous areas of the body, including, without limitation, the face (especially the region between the nose and upper lip), forehead, lips, neck, arms, hands, legs, knees, feet, chest, back, groin, buttocks, thighs, and the like. In another embodiment, the compositions are applied to the face.

As commonly known, the skin is composed of multiple layers of cells, which may be broadly divided into two sections—the top epidermis and the underlying dermis layers.

Epidermis

The epidermis is the top most layer of the skin that provides waterproofing and serves as a barrier to infection and other external elements. This layer mostly consists of keratinocyte cells, which originate in the basal layer (the deepest layer of the epidermis) from the division of keratinocyte stem cells. The keratinocytes push up through the layers of the epidermis, undergoing gradual differentiation. While these cells move to the surface of the skin the keratinocytes are enucleated, flattened and highly keratinized. Eventually the keratinocytes die off and form the stratum corneum (the outermost layer of the epidermis), which serves as an effective barrier against the entry of foreign matter and infectious agents into the body and minimizes moisture loss. In normal and healthy skin, keratinocytes are shed and replaced continuously every 30 days. Whereas, in aging skin, the stratum corneum loses its capacity to retain moisture as the rate of keratinocyte renewal is reduced, and the skin dehydrates.

Dermis

The dermis is the underlying layer of the skin located between the epidermis and subcutaneous tissue. It is the thickest of the skin layers and comprises the extracellular matrix of the skin, which is maintained by fibroblast cells. Fibroblasts maintain the structural integrity of connective tissues by continuously secreting precursors of the extracellular matrix. In the aging skin, the fibroblasts which ensure a balance between the synthesis and maturation of both the collagen and elastin fibres, and their breakdown, tip this equilibrium towards the breakdown of collagen and elastin fibres.

Melanocytes and Skin Pigmentation

Skin and hair pigmentation is determined by the level of melanin present in the epidermis and hair fiber, respectively. For example, three different types of melanin are present in the epidermis: DHI-melanin, DHICA-melanin and pheomelanin. The different types of melanin vary in color or shade. DHI-melanin is the darkest and is blackish in color. DHICA-melanin is brownish in color. Pheomelanin is the lightest and is reddish in color.

Melanin, as described above, is synthesized in specialized organelles called melanosomes within pigment-producing cells (melanocytes). Melanocytes respond to stimuli and regulate melanin synthesis. Melanogenesis is regulated by a variety of environmental and hormonal factors. Melanocytes, which comprise less than 1% of the cells in the epidermis, respond to various signals with alterations in melanin synthesis. Melanin is deposited into organelles known as melanosomes that are transferred to the keratinocytes.

Yeast/*C. borealis* Fermentation Extract

In one embodiment, the natural plant material is, but not limited to, a yeast/*C. borealis* fermentation extract, including components or extracts derived therefrom, which stimulates fibroblast and keratinocyte proliferation, increases the expression of collagen, and inhibits collagenase activity, such that when a composition having the natural plant material is administered topically to skin affected by aging or environmental stress, the condition and aesthetic appearance of the skin affected by dermatological signs of aging are improved, e.g., by lessening facial lines, wrinkles, and sagging skin. Collaterally, there is an improvement is the aesthetic appearance of the aging skin evidenced by an increase in one or more of skin firmness, skin plumpness, skin suppleness, or skin thickness. The topical composition is applied daily and remains on the affected area.

As disclosed herein, a topical composition may comprise at least one yeast/*C. borealis* fermentation extract in an amount sufficient to stimulate fibroblast proliferation, stimulate keratinocyte proliferation, increase the expression of collagen, inhibit collagenase activity, decrease melanin production in melanocytes, block or slow transport of melanin from melanocytes to other cells, or any combination thereof together with a cosmetically, dermatologically, pharmaceutically, or physiologically acceptable vehicle.

The yeast/*C. borealis* ferment extract of the present invention is obtained through a specialized process called fermentation. Fermentation occurs when living eukaryotic and/or prokaryotic microorganisms are grown on a nutrient media either in the presence of oxygen (known as aerobic fermentation) or the absence or diminishment of oxygen (known as anaerobic fermentation). The fermentation process can take place with one microorganism, or simultaneously or sequentially with two or more microorganisms (often referred to as co-ferments). The nutrient media is typically a well-defined mixture of proteins, sugars, minerals and the like. Such media is known to a person skilled in the art and may be available through a variety of commercial sources.

The process of metabolizing yeast can occur with a variety of microorganisms such as, for example, yeast, *bacillus*, molds, plant cells and the like. Especially one embodiment for the composition of the present invention are ferments made using yeast. As used herein, the term "yeast" is meant to encompass a single yeast cell, multiple yeast cells and/or a culture of yeast cells. The yeast of the present invention can be of various fungal families, known to those skilled in the art including, but not limited to: *Neurospora, Ceratostomella, Claviceps, Xylaria, Rosellinia, Helotium, Sclerotinia, Tulostoma, Rhizopogon, Truncocolumella, Mucor, Rhizopus, Entomophthora, Dictostylium, Blastocladia, Synchytrium, Saprolegnia, Peronospora, Albugo, Pythium, Phytophthora, Plasmodiophora, Tuber, Hydnum, Lecanora, Roccella, Pertusaria, Usnea, Evernia, Ramalina, Alectoria, Cladonia, Parmelia, Cetraria, Agaricus, Cantharellus, Omphalotus, Coprinus, Lactarius, Marasmius, Pleurotus, Pholiota, Russula, Lactarius, Stropharia, Entoloma, Lepiotaceae, Corticium, Pellicularia, Tricholoma, Volvaria, Clitocybe, Flammulina, Saccharomyces, Schizosaccharomyces, Saccharomycetaceae, Eurotium, Aspergillus, Thielavia, Peziza, Plectania, Morchella, Wynnea, Helvella, Gyromitra, Phallales, Dictyophera, Mutinus, Clathrus, Pseudocolus, Lycoperdon, Calvatia, Geastrurm, Radiigera, Astreus, Nidularia, Gastrocybe, Macowanites, Gastroboletus, Albatrellus, Neolentinus, Nigroporus, Oligoporus, Polyporus, Fistulina, Fomes, Boletus, Fuscoboletinus, Leccinum, Phylloporus, Suillus, Strobilomyces, Boletellus, Tremella, Auricularia, Dacrymyces, Melampsora, Cronartium, Puccinia, Gymnosporangium, Tilletia, Urocystis, Septobasidiurm, Hygrocybe, Hygrophorus, Hygrotrama, Neohygrophorus, Cortinarius, Gymnopiluis, Trichophyton, Microsporum, Monilia, Candida, Cercosporella, Penicillium, Blastomyces, Cercospora, Ustilaginoidea, Titbercularia, Fusariurm, Rhizoctinia, Ozoniurm, Sclerotiurm, Geoglossum,* or *Armillaria*. In one embodiment, fungi of interest are the fungi belonging to the family Saccharomycetaceae. In another embodiment, of interest are the fungi belonging to the genus *Pichia*. In another embodiment, of interest are the fungi belonging to the species pastoris. In one embodiment, *Pichia pastoris* is used in the fermentation process.

Typically, yeasts belonging to the phylum Ascomycetes are facultative anaerobes; that is they can grow both in the presence or absence of oxygen. For the purpose of the present invention, yeast was aerobically grown and therefore air is critical for growth.

The yeast/*C. borealis* extracts of the present invention include cytoplasmic and extra-cellular components of the yeast which include, but are not limited to, the nutrient broth, cellular protein material, cellular nucleic material, cellular protoplasmic material and/or cell wall components. Typically, the extracts are relatively water soluble, for example, equal or more than 1-gram of yeast extracts dissolve in 1-gram of water. The extracts may also be soluble in water/organic solvent mixtures such as, but not limited to, aqueous glycols and aqueous glycerols.

The yeast fermentation process can be carried out in a stirred tank bio-reactor. Examples of such bioreactors might include for example, fermentors available from New Brunswick Scientific, Edison N.J. or Applikon Biotechnology Foster City Calif.

To produce a yeast/*C. borealis* fermentation extract of the present invention, *Pichia pastoris* cell culture can be grown between 25.degree. C. to 32.degree. C. in a growth media. An example of a typical yeast fermentation media can be typically found in the "Handbook of Microbiological Media" published by CRC press. For the purpose of this invention, a specific growth media for fermentation of yeast is used. This growth media is chemically defined media and does not have any animal-derived products. In a one embodiment, the sole source of carbon in the media of present invention is from glycerol.

The yeast/*C. borealis* fermentation extract can be obtained by first separating the bio-mass and then extracting active ingredients from the extra-cellular secretions of the yeast. Alternatively, the yeast cell can be lysed to obtain yeast/*C. borealis* ferment lysate by processes known to those skilled in the art. Typically, the process involves the rupture of the yeast cell walls by chemical, enzymatic or physical means or by combination of these. The yeast/*C. borealis* ferment extract may be further purified by chromatography, solvent extraction, centrifugation, decantation, filtration or carbon treatment, or other means known to a person skilled in the field. In one embodiment, the yeast/*C. borealis* ferment extract is further concentrated by any means known to those skilled in the art, for example, evaporation, spray-drying, lyophylization, belt or drum drying.

After exposing the yeast, for example, *Pichia pastoris*, to *C. borealis* growth factor during a key phase of the fermentation process, the yeast has significant genomic and proteomic changes compared to the yeast that is not subjected to the treatment of the *C. borealis*. In addition, examination of yeast microarrays indicates that various genes within the fermenting *pichia pastoris* are either upregulated or downregulated as a result of treatment with the *C. borealis*. The terms upregulated and downregulated refer to the influence the *C. borealis* has on signalling genes within the yeast to either be turned-on (upregulated) or turned-off (downregulated). The up and down-regulation of the yeast genes can result in changes in protein expression which allows the yeast to express proteins that would not normally be expressed if the *C. borealis* were not present.

In addition, the *Pichia pastoris* may ingest the *C. borealis* and begin to convert the *C. borealis* into chemical derivatives such as, for example, sugar or protein derived metabolites of *C. borealis*. The yeast might do this as a means to begin the process of digesting the *C. borealis*. In one embodiment, if the yeast chemically attaches a protein to the *C. borealis* on one of the available hydroxyl groups on *C. borealis*, such molecules might appear in 2D-gel electrophoresis as new proteins. It is difficult to differentiate these new chemically altered *C. borealis* molecules from normal metabolic proteins that the yeast typically expresses. However, some techniques such as MALDI-TOF Mass Spectroscopy can be used to identify proteins from 2D-gels. In addition, one can examine protein and sugar metabolites of *C. borealis* by high performance liquid chromatography (HPLC). Without being bound by theory, it is believed that the secondary metabolites of *C. borealis* formed by fermentation may play a significant role in the ability of the yeast/*C. borealis* ferment extract to stimulate human skin in beneficial ways not available to just the yeast or the *C. borealis* alone.

In one embodiment, the yeast is fermented with the *C. borealis* extract for a period of between about 72 and about 140 hours. In one embodiment, the *C. borealis* extract is fed to the yeast 1-2 days after the yeast reaches logarithmic growth phase. In another embodiment, the yeast/*C. borealis* fermentation extract comprises a mixture of oligosaccharides, proteins, and glycosylated sugars that are obtained from both the yeast and *C. borealis* during fermentation. In another embodiment, the yeast/*C. borealis* fermentation extract comprises a partially metabolized mixture with remaining, unmetabolized *C. borealis* extract. In another embodiment, the *C. borealis* extract utilized is derived from the root of the *C. borealis* plant.

The effect of the yeast/*C. borealis* ferment extract to influence human skin can be measured in a number of ways known to those skilled in the art. In one embodiment, the yeast/*C. borealis* fermentation extracts can be screened for their effects on skin by employing analytical techniques such as, for example, human genomic microarrays on specific skin cells such as keratinocytes or fibroblasts, or by protein expression analysis on individual skin cells, tissue models or ex vivo or in vivo skin models. In these testing models, specific genes and or proteins may be up-regulated or down-regulated as a result of the extract treatment. Genes and proteins that are capable of regulating skin conditions are one embodiment of interest. In one embodiment of interest for the purpose of the present invention are genes and proteins related to extracellular matrix expression, melanin regulation, skin moisturization, exfoliation and the like. In one embodiment interest are proteins related to cyclooxygenase expression, in one embodiment cyclooxygenase-1 and 2 and also extracellular matrix protein expression, in one embodiment, types, I, IV and VI collagen expression. In addition, the influence of the extract on skin melanin expression is also of considerable interest.

The effect of the yeast/*C. borealis* ferment extract on expression of these and other important cutaneous proteins can be monitored by human genomic microarray analysis and protein expression as well as by non-invasive test methods well-known to those in skilled in the art, including, but not limited to, improved moisturization, wrinkle reduction, reduced pigmentation, improved skin tone and the like. Application of the yeast/*C. borealis* ferment extract can result in measured reductions in skin wrinkles, for example, as measured by techniques such as SilFlo silicone modeling, PRIMOS and VISIO photographic systems and the like. In addition, moisturization might be measured using transepidermal water loss (TEWL) or cutometer or corneometric measurements. Likewise, skin pigmentation could be measured using a chromometer. Such testing technologies are well-known to those skilled in the art and can be found in Handbook of non-invasive methods and the skin, 2.sup.nd edition, Serup J, Jemec G B E, Grove G L (ed.), Taylor and Francis Boca Raton Fla. 2006, the disclosure of which is incorporated herein by reference in its entirety.

Yeast/botanical extracts are commercially available, for example the Metabiotics line of yeast extracts sold by Arch Personal Care Products, L.P., South Plainfield, N.J.

In one embodiment, the yeast/*C. borealis* fermentation extract has been newly found to provide treatment for lightening skin, thickening skin, reducing hirsuteness and/or otherwise driving a phenotype change from non-palmoplantar to palmoplantar skin by increasing the expression of DICK-KOPF-1. These yeast/*C. borealis* fermentation extracts have been newly determined to be effective anti-aging or prophylactic agents in compositions and methods for reducing signs of aging. Specifically, the yeast/*C. borealis* fermentation extracts, which increase proliferation of fibroblasts and keratinocytes, cell-cell adhesion in the epidermis and dermis, cell nourishment to the epidermis, cell-cell anchoring and adhesion between keratinocytes, communication between the dermis and epidermis, collagenase overproduction, collagen expression, and mechanical properties of the skin, alleviate the dermatological signs of chronologically or hormonally-aged or photo-aged skin, such as fine lines, wrinkles, and sagging skin, and other conditions due to a progressive degradation of the skin cell growth, proliferation and functionality in the epidermal and dermal layer.

The composition comprising these yeast/*C. borealis* fermentation extracts are effective when topically applied, in a daily manner. Without wishing to be bound by theory, the yeast/*C. borealis* fermentation extracts decrease pigmentation; lighten skin; treat hyperpigmented skin; increase skin thickness; reduce skin hirsuteness; and/or change skin phenotype from non-palmoplantar to palmoplantar by upregulating DICKKOPF-1 expression. Topical application of the yeast/*C. borealis* fermentation extracts also facilitates the targeted delivery of active components without the requirement of an injection or the expertise of a health practitioner.

As disclosed herein, the compositions have a concentration of yeast/*C. borealis* fermentation extract of from about 0.0001 wt % to about 90 wt %, about 0.001 wt % to about 25 wt %, about 0.01 wt % to about 10 wt %, about 0.01 wt % to 5 wt %, about 0.05 wt % to about 1%, and about 0.05 wt % to about 0.5 wt %, based on the total weight of the composition. One of ordinary skill in the art would be able to adjust the amount of extract used based upon the specific application or effect desired.

In one embodiment, the yeast/*C. borealis* fermentation extracts of the present disclosure may be contained in a cosmetically or dematologically acceptable vehicle, medium, diluent or carrier. In an embodiment embracing topical application, the compositions of this disclosure comprise a medium (vehicle, diluent or carrier) that is compatible with human skin. The compositions can be formulated as aqueous, alcohol, or aqueous/alcohol-based solutions, ointments, lotions, gels, water-in-oil, oil-in-water, of water-oil-water triple emulsions having the appearance of a cream or gel, microemulsions, or aerosols. In addition, the compositions can be in the form of vesicular dispersions containing ionic and/or nonionic lipids, as described above. Dosage units suitable for such compositions are formulated according to the conventional knowledge and techniques used in the art.

Methods of Using Natural Plant Materials

In one embodiment, the present invention encompasses a method of improving the condition and aesthetic appearance of skin, comprising applying to an affected area of skin, a composition containing a yeast/*C. borealis* fermentation extract, in order to decrease pigmentation; lighten skin; treat hyperpigmented skin; increase skin thickness; reduce skin hirsuteness; and/or change skin phenotype from non-palmoplantar to palmoplantar.

Another embodiment relates to the use of the topical composition as an anti-aging prophylactic agent for improving the condition and aesthetic appearance of skin and comprises applying to the skin, or introducing via a directed mode of delivery, a composition including yeast/*C. borealis* fermentation extract, alone or in combination with one or more additional natural plant extracts, in an amount effective to improve the aesthetic appearance of conditions related to skin, where the yeast/*C. borealis* fermentation extract decreases pigmentation; lightens skin; treats hyperpigmented skin; increases skin thickness; reduces skin hirsuteness; and/or changes skin phenotype from non-palmoplantar to palmoplantar.

In a specific embodiment, an extract of yeast/*C. borealis* extract is provided in a pharmaceutically, physiologically, cosmetically, and dermatologically acceptable vehicle, diluent, or carrier, where the composition is topically applied to an affected area of skin in need of treatment, e.g., applied to a wrinkle, or to thinning skin, or to sagging skin, and left to remain on the affected area in an amount effective for treatment for the dermatological signs of aging and improving the condition and aesthetic appearance of skin. Typically, the composition is applied to the skin as a thin film to affected skin to be treated, and often will apply the composition to other areas of the skin prophylactically.

As will be appreciated by the practitioner, cosmetic treatments comprising compositions containing yeast/*C. borealis* fermentation extracts, including extracts, components, and/or constituents of the invention may be carried out, for example, by topically applying the cosmetic composition as described herein according to the routine technique for administering such compositions. The topical cosmetic composition is typically applied once or twice daily (e.g., morning and evening) for a period of at least one week, but may include a period of about 2, 4, 8, or 12 weeks. The consumer may wish to continue use of the composition for an extended period of time. The cosmetic composition is applied to the face and neck, but may be applied to any area of skin in need of aesthetic improvement, where the cosmetic composition remains on the affected area of skin, and not removed or rinsed off the skin Routine and commonly practiced techniques encompass the application of creams, lotions, gels, masks, sera, ointments, patches, makeup, makeup-removing milks, sunscreen compositions, or the like, to the skin. The cosmetic composition is a topical leave on formulation, where spraying as a form of application is also envisioned.

In one embodiment of the invention, the topical compositions having a natural plant material such as but not limited to, Yeast/*C. borealis* extract, including components or extracts derived therefrom, are useful for improving the condition and aesthetic appearance of skin affected by aging, in one embodiment matured or maturing skin, by anyone of the following methods: reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and in one embodiment deep wrinkles or creases; preventing, reducing, and/or diminishing the appearance and/or depth of lines and/or wrinkles; improving the appearance of suborbital lines and/or periorbital lines; improvement in appearance of skin contours, hollow cheeks, sunken eyes, reducing the appearance of crow's feet; rejuvenating and/or revitalizing skin, in one embodiment aging skin; reducing skin fragility; ameliorating the effects of estrogen imbalance; preventing and/or treating skin atrophy; improving skin tone tautness; preventing, reducing, and/or ameliorating skin sagging; preventing, reducing, and/or ameliorating thinning skin, improving skin firmness, plumpness, and/or suppleness; improving procollagen and/or collagen production; improving skin texture and/or promoting retexturization; improving skin barrier repair and/or function; improving the appearance of skin contours; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; increasing skin elasticity and/or resiliency; enhancing exfoliation; improving microcirculation; decreasing and/or preventing cellulite formation; decreasing pigmentation; lightening skin; treating hyperpigmented skin; increasing skin thickness; reducing skin hirsuteness; and/or changing skin phenotype from non-palmoplantar to palmoplantar; and any combinations thereof.

Second Active Agent

The compositions of the present invention may include, in addition to the yeast/*C. borealis* extract, one or more active skin treatment agents agents.

Suitable other skin treatment actives to include the compositions disclosed herein include, but are not limited to: *Abies pindrow* extract, *Acacia catechu* extract, *Anogeissus latifolia* extract, *Asmunda japonica* extract, *Azadirachta indica* extract, *Butea frondosa* extract, *Cedrus deodara* extract, *Emblica officinalis* extract, *Ficus benghalensis* extract, *Glycyrrhiza glabra* extract, *Ilex purpurea Hassk* extract, *Innula racemosa* extract, *Ligusticum chiangxiong* extract, *Ligusticum lucidum* extract, *Mallotus philippinensis* extract, *Mimusops elengi* extract, *Portulaca oleracea* extract, *Portulaca sativa* extract, *Atriplex portulacoides* extract, *Morinda citrifolia* extract, *Moringa oleifera* extract, *Naringi crenulata* extract, *Nerium indicum* extract, *Psoralea corylifolia* extract, *Stenoloma chusana* extract, *Terminalia bellerica* extract, tomato glycolipid, *Amorphophallus campanulatus* extract, *Olisma orientale* extract, *Plumbago indica* extract, *Cananga odorata* extract, *Sapindus rarak* extract, *Curcuma xanthorrhiza* extract, *Physalis minima* extract, *Stephania rotunda* extract, *Rhinacanthus nasutus* extract, *Humulus scandens* extract, *Sesbania grandiflora* extract, *Pouzolzia pentandra* extract, *Piper betel* extract, *Jasminum sambac* extract; *Eliptica prostrata Linn* extract; *Clitoria tematea Linn* extract; *Ozothamnus obcordatus* extract; *Erythrina flabelliformis* extract; *Lonchocarpus capassa* extract; *Sophora tomentosa* extract; Tetrandrine; Carvacrol; Retinyl punicate; MycoFusions Coriolus Black Corn Biomass; MycoFusions Maitake Waxy Hulless Barley Biomass; *Zanthoxylum nitidium* extract; Ophiopogon Thunb. P.E. extract; *Radix platycodonis* extract; and *Cocculus glaucescens* extract; paxillin; *Coccinia grandis* extract; *Trifolium hybridum* extract; *Eremophila mitchellii* extract; *Kunzea ambigua* extract; Tanshinone HA; Tetrandrine; Carvacrol; cis-6-Nonenol; Retinyl punicate; Retinyl oleate; Equol; *Terminalia belerica* extract; Stephania solid extract; and Rosemary extract, L-4-thiazolylalanine, tetramethylpyrazine, (2S,3S)-3-amino-2-hydroxy-4-phenylbutanoic acid, 3-hydroxy-4,5-dimethylfuran-2(5H)-one, black cohosh, *Cimicifuga racemosa* extract, *Capsicum amuum* extract, cedar, Derris Scandens Benth extract, *Erythrina flabelliformis* extract, *Withania somniferia* extract, fir needle (*Abies alba*), *Helichrysum gymnocephalum* extract, holly (Ilex) extract, laurel clock vine (*Thunbergia laurifloria*) extract, *Leptospermum lanigerum* extract, *Grifola frondosa* extract, *Melicope hayesii* extract, Norway spruce, *Phyllarthron bojeranum* extract, pine needles, *Piper nigrum* extract, *Sophora tomentosa* extract, spruce needles, *Thuja* extract, 1-aroyl-N-(2-oxo-3-piperidinyl)-2-piperazine or a cosmetically acceptable salt thereof, desthiobiotin, and compatible combinations thereof.

Other second active agents may include other yeast fermentation products when yeast (for example, *Pichia pastoris*) is fermented (optionally while stressed) with active agents. Such second active agents include those described in U.S. Patent Publication Serial No. 2011/0052517, herein incorporated by reference in its entirety for all purposes. Examples of methods of preparing such second active agents may be found, for example, in U.S. Patent Application Publication Serial No. 2010/0021532, herein incorporated by reference in its entirety for all purposes.

Other second active agents may include, without limitation, botanicals (e.g., as described above); phytol; ascorbic acid and its derivatives, thiodipropionic acid (TDPA) and esters thereof; retinoids (e.g., 9-cis retinoic acid, 13-cis retinoic acid, all-trans retinoic acid and derivatives thereof, phytanic acid, retinol (Vitamin A) and esters thereof, such as retinol palmitate, retinol acetate and retinol propionate, and salts thereof and others); hydroxy acids (including alpha-hydroxyacids and beta-hydroxyacids), salicylic acid and alkyl salicylates; exfoliating agents (e.g., glycolic acid, 3,6, 9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof, etc.), to name a few. Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

Other second active agents may include tocopheryl acetate; carrot (*Daucus carota* sativa); soybean and soybean extracts; algae (*Phaeodactylum tricornutum*) and extracts thereof; gamma oryzanol; kudzu (*Pueraria lobate*) and extracts thereof; tetrahexyldecyl ascorbate; and *Saxifraga sarmentosa* and extracts thereof.

Vehicle and Compositions

In accordance with this disclosure, the compositions containing the yeast/*C. borealis* extract can further include antioxidants, anti-inflammatories, sunscreens, cosmetics, including make-ups, anti-aging formulations, e.g., creams for fine lines and/or wrinkles, topicals, skin penetration enhancers, sprays, and the like. Also in accordance with this disclosure, the plant components and additional ingredients comprising such compositions can be formulated in a variety of product forms. The compositions may be prepared in targeted delivery systems, e.g. creams, lotions, gels, serums, transdermal patches, and the like, in one embodiment for topical administration. Targeted delivery and/or penetration enhancement may also be achieved by iontophoresis.

The present disclosure further provides the compositions comprising the plant components for topical administration or for targeted delivery without inducing significant irritation. Thus, the inventive compositions are especially suitable for sensitive skin The compositions are applied to the skin for a period of time sufficient to improve the aesthetic appearance of skin. The compositions are applied topically once, twice, or more daily, once daily. The daily application is for a period of one week, two weeks, four weeks, or more. The compositions can be formulated into liposomes which can comprise other additives or substances, and/or which can be modified to more specifically reach or remain at a site following administration.

The present disclosure encompasses compositions comprising a cosmetically or dermatologically acceptable formulation which is suitable for contact with living animal tissue, including human tissue, with virtually no adverse physiological effect to the user. Compositions embraced by this disclosure can be provided in any cosmetically and/or dermatologically suitable form, as a lotion or cream, but also in an anhydrous or aqueous base, as well as in a sprayable liquid form. Other suitable cosmetic product forms for the compositions of this disclosure include, for example, an emulsion, a lip balm, a lip gloss, a lotion, a mask, an ointment, a mousse, a patch, a pomade, a solution, a spray, a wax-based stick, or a towelette. In addition, the compositions contemplated by this disclosure can include one or more compatible cosmetically acceptable adjuvants commonly used and known by the skilled practitioner, such as colorants, fragrances, emollients, humectants, preservatives, vitamins, chelators, thickeners, anesthetics, anti-allergenics, antifungals, antimicrobials, other anti-inflammatory agents, antioxidants, antiseptics, depigmenting agents, film formers, insect repellents, pharmaceutical agents, photostabilizing agents, sunscreens, stabilizers, surfactants, thickeners, viscosity modifiers, and the like, as well as other botanicals such as aloe, chamomile, and the like, and as further described below.

Cosmetically or dermatologically acceptable vehicles that can be used in the present topical compositions include, but are not limited to, one or more aqueous systems, glycerins, $C_{1-4}$ alcohols, fatty alcohols, fatty ethers, fatty esters, polyols, glycols, vegetable oils, mineral oils, liposomes, laminar lipid materials, silicone oils, water or any combinations thereof.

In the present disclosure, the vehicle may be in the form of an aqueous phase, an oil phase, a gel, a wax-in-water emulsion, a silicone-in-water emulsion, a water-in-silicone, an oil-in-water emulsion, or a water-in-oil emulsion. The aqueous phase is a mixture of one or more water soluble or water dispersible ingredient, which can be liquid, semi-solid or solid at room temperature (25.degree.C). The vehicle comprises or can be in the form of a suspension, dispersion or solution in water or an aqueous-alcoholic vehicle, which may contain a thickener or gellant. A person skilled in the art can select the appropriate product form, the ingredients contained therein, as well as the method for preparing it, on the basis of the knowledge that the skilled artisan possesses.

The composition may include or be an aqueous phase which may contain water or a mixture of water and at least one hydrophilic organic solvent such as an alcohol, especially a linear or branched lower monoalcohol containing from 2 to 5 carbon atoms, e.g., ethanol or propanol; a polyol, e.g., propylene glycol, sorbitol, glycerol, diglycerol, panthenol, or polyethylene glycol, and mixtures thereof. This aqueous phase may represent from about 0.5 to about 99.99 wt % by weight of the composition. In one embodiment, the yeast/*C. borealis* extract is soluble in water.

When the composition of the disclosure is in the form of an emulsion, it can also optionally comprise a surfactant, in an amount of from 0.1 to 30% and in one embodiment from about 1 to about 20 wt % by weight of the composition.

The composition may be or comprise a thickening polymer such as an amphiphilic polyurethane, a polyacrylic homopolymer or copolymer, a polyester, and/or a hydrocarbon-based resin. The polymers can be dissolved or dispersed in the cosmetically acceptable vehicle and optionally combined with a plasticizer.

The composition of the disclosure may also comprise an oil phase containing oil soluble or oil dispersible ingredients that are liquid at room temperature (25.degree. C.) and/or oily or waxy substances that are solid at room temperature, such as waxes, semisolids, gums, and mixtures thereof. This oily phase may also contain organic solvents.

Suitable oily materials that are liquid at room temperature, often referred to as oils, include hydrocarbon-based oils of animal origin such as perhydrosqualene; hydrocarbon-based plant oils such as liquid triglycerides of fatty acids of 4 to 10 carbon atoms, for instance, heptanoic or octanoic acid triglycerides, or oils such as sunflower oil, corn oil, soybean oil, grapeseed oil, castor oil, avocado oil, caprylic/capric acid triglycerides, jojoba oil; linear or branched hydrocarbons of mineral or synthetic origin such as liquid paraffins and derivatives thereof, petroleum jelly; synthetic esters and ethers, in one embodiment esters of fatty alcohols, namely; for example, isopropyl myristate, 2-ethylhexyl palmitate, 2-octyldodecyl stearate, isostearyl isostearate; hydroxylated esters such as isostearyl lactate, octyl hydroxystearate, octyldodecyl hydroxystearate, heptanoates, octanoates and decanoates of fatty alcohols; polyol esters such as propylene glycol dioctanoate, neopentyl glycol diheptanoate, diethylene glycol diisononanoate, and pentaerythritol esters; fatty alcohols containing from 12 to 26 carbon atoms such as octyldodecanol, 2-butyloctanol, 2-hexyldecanol, 2-undecylpentadecanol, oleyl alcohol; partially hydrocarbon-based fluoro oils and/or fluorosilicone oils; silicone oils such as volatile or non-volatile, linear or cyclic polymethylsiloxanes (PDMS) that are liquid or semisolid at room temperature such as cyclomethicones and dimethicones, optionally comprising a phenyl group, for instance phenyl trimethicones, siloxanes, and mixtures thereof. These oils are usually present in an amount of 0 wt % to about 90 wt %, from about 1 wt % to 80 wt % by weight of the oil phase.

The oil phase of the composition of the disclosure may also comprise one or more cosmetically acceptable organic solvents. These solvents are present in an amount of 0 wt % to about 60 wt %, about 1 wt % to 30 wt % by weight of the composition and can be selected from the group consisting of lipophilic organic solvents, amphiphilic organic solvents and mixtures thereof. Suitable solvents which can be used in the composition of the disclosure include acetic acid esters such as methyl, ethyl, butyl, amyl or 2-methoxyethyl acetate; isopropyl acetate; hydrocarbons such as toluene, xylene, p-xylene, hexane or heptane; ethers containing at least 3 carbon atoms, and mixtures thereof.

The composition of the disclosure may further comprise any ingredient conventionally used in the cosmetic field. These ingredients include preserving agents, aqueous phase thickeners (polysaccharide biopolymers, synthetic polymers) and fatty-phase thickeners, fragrances, hydrophilic and lipophilic active agents, and mixtures thereof. The amounts of these various ingredients are those conventionally used in the cosmetic field to achieve their intended purpose, and range typically from about 0.01 wt % to about 20 wt % by weight of the composition. The nature of these ingredients and their amounts must be compatible with the production of the compositions of the disclosure.

The composition of the disclosure may also comprise an additional particulate phase, typically present in an amount of 0 wt % to about 30 wt % by weight of the composition, from about 0.05 wt % to about 20 wt %, and which can comprise pigments and/or pearlescent agents and/or fillers used in cosmetic compositions. Suitable inorganic pigments include titanium oxide, zirconium oxide and cerium oxide, as well as zinc oxide, iron oxide, chromium oxide and ferric blue. Suitable organic pigments include barium, strontium, calcium, and aluminium lakes and carbon black. Suitable pearlescent agents include mica coated with titanium oxide, with iron oxide, or with natural pigment. Fillers are normally present in an amount of 0 to about 20 wt. % by weight of the composition, about 0.1 to about 10 wt %. Suitable fillers include talc, silica, zinc stearate, mica, kaolin, nylon (in one embodiment orgasol) powder, polyethylene powder, Teflon, starch, boron nitride, copolymer microspheres such as Expancel (Nobel Industrie), Polytrap (Dow Corning), and silicone resin microbeads (Tospearl from Toshiba).

The oil phase of the compositions of the disclosure may comprise one or more waxes, gums, or mixtures thereof. The waxes include hydrocarbon-based waxes, fluoro waxes and/or silicone waxes and can be of plant, mineral, animal and/or synthetic origin. In one embodiment, the waxes have a melting point of greater than 25° C., greater than 45° C. The compositions of the present disclosure may contain from 0 to about 20 wt % waxes by weight of the composition. The gums are generally high molecular weight PDMSs or cellulose gums or polysaccharides and the semisolid materials are generally hydrocarbon-based compounds such as lanolins and derivatives thereof or alternatively PDMSs. The compositions of the present disclosure may contain from 0 to about 20 wt % gums by weight of the composition, typically from about 0.1% wt to about 10 wt %.

Another embodiment of the present disclosure is directed to the delivery of the described compositions by the use of targeted delivery systems, for example, liposomes, microspheres (see, e.g., U.S. Pat. No. 5,770,222 to Unger et al.), and the like, so that the components and/or active constituents can more readily reach and affect the subcutaneous layer of the area of application, e.g., face or neck, or the other area of the skin In another embodiment, the topical compositions of the present disclosure also include at least one of the following: a skin penetration enhancer, a surface smoother, a skin plumper, an optical diffuser, a sunscreen, an exfoliation promoter, and an antioxidant. Details with respect to these and other suitable cosmetic ingredients can be found in the "International Cosmetic Ingredient Dictionary and Handbook," 10th Edition (2004), published by the Cosmetic, Toiletry, and Fragrance Association (CTFA), at pp. 2177-2299, which is herein incorporated by reference in its entirety.

A sunscreen protects the skin from damaging ultraviolet rays. In an illustrative embodiment of the present disclosure, the sunscreen would provide both UVA and UVB protection, by using either a single sunscreen or a combination of sunscreens. Among the sunscreens that can be employed in the present compositions are avobenzone, cinnamic acid derivatives (such as octylmethoxy cinnamate), octyl salicylate, oxybenzone, titanium dioxide, zinc oxide, or any mixtures thereof. The sunscreen may be present from about 1 wt % to about 30 wt % of the total weight of the composition. The addition of a sunscreen may prevent/reduce the photodegradation of the composition while in the package as well as serve to protect the skin from ultraviolet radiation.

The compositions of the present disclosure having sunscreen bring about additional improvements to the aesthetic appearance of skin, including at least one of the following: minimizes sunburning, minimizes tanning, and reduces redness.

An antioxidant functions, among other things, to scavenge free radicals from skin to protect the skin from environmental aggressors. Examples of antioxidants that may be used in the present compositions include compounds having alpha hydroxy acids (AHA); benzoyl peroxide; beta hydroxy acids; keto acids, such as pyruvic acid, 2-oxopropanoic acid, 2-oxobutanoic acid, and 2-oxopentanoic acid; oxa acids as disclosed in U.S. Pat. Nos. 5,847,003 and 5,834,513 (the disclosures of which are incorporated herein by reference); salicylic acid; urea; or any mixtures thereof. The anti-oxidants are 3,6,9-trioxaundecanedioic acid, glycolic acid, lactic acid, or any mixtures thereof; phenolic hydroxy functions, such as ascorbic acid and its derivatives/esters; beta-carotene; catechins; curcumin; ferulic acid derivatives (e.g. ethyl ferulate, sodium ferulate); gallic acid derivatives (e.g. propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present disclosure may have an antioxidant from about 0.001 wt % to about 10 wt %, and more from about 0.001 wt % to about 5 wt %, of the total weight of the composition.

The present composition may also have one or more of the following active agents, ingredients or adjuvants: anesthetics, anti-allergenics, antifungals, antiseptics, chelating agents, colorants, demulcents, emollients, emulsifiers, fragrances, humectants, lubricants, moisturizers, pH adjusters, pigment altering agents, preservatives, stabilizers, surfactants, thickeners, viscosity modifiers, vitamins, or any mixtures thereof. The amounts of these various substances are those that are conventionally used in the cosmetic or pharmaceutical fields, for example, they can constitute from about 0.01% to about 20% of the total weight of the composition.

Non limiting examples of active agents for formulating into the compositions of the present disclosure include those reagents having an effect on the treatment of wrinkles and/or fine lines, in addition to the natural plant actives as described, such as keratolytic agents, i.e., an active agent having desquamating, exfoliant, or scrubbing properties, or an active agent which can soften the horny layer of the skin. Other examples of anti-wrinkle or anti-fine line active agents include hydroxy acids and retinoids. These agents can be formulated, for example, in amounts of from about 0.0001% to about 5% by weight relative to the total weight of the composition.

Suitable hydroxy acids include, for example, glycolic acid, lactic acid, malic acid, tartaric acid, citric acid, 2-hydroxyalkanoic acid, mandelic acid, salicylic acid and alkyl derivatives thereof, including 5-n-octanoylsalicylic acid, 5-n-dodecanoylsalicylic acid, 5-n-decanoylsalicylic acid, 5-n-octylsalicylic acid, 5-n-heptyloxysalicylic acid, 4-n-heptyloxysalicylic acid and 2-hydroxy-3-methylbenzoic acid or alkoxy derivatives thereof, such as 2-hydroxy-3-methyoxybenzoic acid.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

In one embodiment, the compositions for topical application can be in the form of a protective care composition for the skin, for the face, the neck, the hands, the feet, or other areas of the body. Non-limiting examples include day creams or lotions, night creams or lotions, sunscreen creams, lotions, or oils, body milks, makeup (a foundation), artificial tanning compositions, depilatories, and patches.

Emulsifiers are typically present in emulsion compositions of the disclosure in an amount of about 0.1% to about 30%, by weight and from about 0.5% to about 30% by weight relative to the total weight of the composition. However, not all compositions will necessarily include emulsifiers.

Hyperpigmentation

In certain embodiments, the cosmetic compositions described herein can be used to treat and/or prevent hyper-pigmentation of skin and/or that of the hair, for example, to lighten skin or hair. In some one embodiment embodiments, a composition comprising an effective amount of a yeast/*C. borealis* fermentation extract is topically applied to the skin or hair, for example to an area of hyper-pigmented skin or hair. Hyper-pigmentation includes any coloration of an individual's skin or hair that is darker than desired by the individual and that is caused by melanocytes. Such unwanted pigmentation may also be called discoloration. Hyper-pigmented areas of the skin include areas of discrete or mottled hyper-pigmentation. Areas of discrete hyper-pigmentation can be distinct, uniform areas of darker color and may appear as brown spots or freckles on the skin, including marks commonly called pigment spots or "age spots." Areas of mottled hyper-pigmentation of the skin can be dark blotches that are larger and more irregular in size and shape than areas of discrete pigmentation. Areas of hyper-pigmentation also include areas of tanned skin, e.g., skin tanned due to UV exposure. Hyper-pigmented hair includes any shade of hair that is darker than desired.

Skin hyper-pigmentation may be caused by any number of factors, including, for example, genetics, UV or sun exposure, age, scarring, or discoloration due to skin injury, including lacerations, burns, sunburn, acne, or other dermatological conditions, and the like. For example, skin hyper-pigmented areas include melasmic patches. Melasma is a common skin disorder involving facial skin discoloration, one embodiment prevalent in pregnant women, where it is called chloasma faciei or chloasma. Melasmic (or chloasmic) patches may appear as dark brown, irregular patches on the face, one embodimently on the upper cheeks, nose, lips, upper lip, and forehead. The patches often develop gradually over time and generally do not itch or otherwise hurt, but may negatively affect an individual's appearance. Skin hyper-pigmentation also refers to areas under the arm, e.g., that have become or are becoming darker than desired.

Skin hyper-pigmentation may or may not include areas under an individual's eyes that are darker than desired by the individual, commonly referred to as "under eye dark circles" or "dark circles." Dark circles are usually round, uniform areas of pigmentation beneath each eye, which may be caused by heredity, allergies, tiredness, or other causes. Treatment of hyper-pigmentation, in some embodiments, excludes treating discoloration and/or bagginess in facial skin below the eyes. Notably, under-eye hyper-pigmentation is not a simple melanocyte-mediated pigmentation problem. Etiologies include circulatory malfunctions, such as increased vascular permeability causing leakage beneath the skin surface, and exposure to the environment, and the problem generally does not respond well to known hypo-pigmenting or skin whitening compounds. Indeed, the topical composition used to reduce under-eye discoloration in that case included a high percentage of ascorbyl phosphate, which itself is a known skin lightener and thus may have been responsible for the under-eye skin lightening. Hyper-pigmented skin may also include skin in the axillary (i.e., underarm) region.

Treating hyper-pigmentation or hyper-pigmented skin/hair refers to eradicating, reducing, ameliorating, or reversing one or more of the unwanted features associated with hyper-pigmentation, such as producing a perceptible lightening of the skin or hair in the affected area. Lightening hyper-pigmented areas of the skin may be desirable, in one embodiment, in diminishing age spots; lightening a suntan; evening or optimizing skin tones, e.g., in areas of mottled hyper-pigmentation; in treating melasmic and chloasmic patches, freckles, after-burn scars, and post-injury hyper-pigmentation. Preventing hyper-pigmentation or hyper-pigmented skin refers to affording skin, not yet affected by hyper-pigmentation, a benefit that serves to avoid, delay, forestall, or minimize one or more unwanted features associated with skin hyper-pigmentation, such as reducing the darkness or size of hyper-pigmented areas that eventually develop.

Yeast/*C. borealis* fermentation extracts that are capable of treating and/or preventing hyper-pigmented skin can be referred to as "skin lighteners." When used for lightening hair, they can be referred to "hair lighteners." In one embodiment, the yeast/*C. borealis* extracts of the present invention are usable to lighten hair in a non-bleaching manner—that is, by suppressing the formation and/or transportation of melanin out of follicular melanocytes, rather than by bleaching the hair itself. In one embodiment, the hair lightened by the instant invention includes facial hair and body hair, s opposed to scalp hair. In one embodiment, the hair lightener is applied to facial hair located on the upper lip.

Pigmentation of the skin (including the lips) and hair is determined by the level and type of melanin present in the epidermis or hair fiber. For example, the greater the epidermal level of DHI-melanin, the darkest type of melanin, the darker the skin. As noted above, melanin is synthesized in specialized organelles called melanosomes within pigment cells (also called pigment-producing cells or melanocytes), and the process begins with the conversion of the amino acid tyrosine to dopaquinone by the enzyme tyrosinase.

Accordingly, another aspect of the instant invention relates to cosmetic use of compositions further comprising a calcium influx inhibitor for skin and/or hair lightening, in addition to the described yeast/*C. borealis* fermentation extract. A "calcium influx inhibitor" as used herein refers to any compound that acts to decrease, reduce, block, or otherwise inhibit the entry of calcium into pigment cells. The term is used interchangeably herein with "calcium channel inhibitor." Calcium influx inhibitors will include compounds known in the art to regulate calcium entry into pigment cells, such as, without limitation, 2-aminoethyl diphenylborate (2-APB). For example, this compound is known to specifically block calcium entry into cells, including into pigment cells. Other known calcium influx inhibitors include, without limitation, Aminohexahydrofluorene, Bepridil, Calcicludine, Calciseptine, Calmidazolium chloride, Nifedipine, Verapamil, FS2 (Dendroaspis polylepis polylepis), Galanin, Protopine, Tetrahydropalmatine, Somatostatin-14, L-Stepholidinealverine and its salts; as well as manganese and its salts, magnesium and it salts. See, e.g., EP 1419764; Int. Pat. Appl. Pub. No. WO 2006048671; and U.S. Pat. Appl. Pub. No. 2009/0028826; and modified stressed yeast extracts, for example as described in U.S. Patent Publication Serial No. 2011/0052517, herein incorporated by reference in their entirety for all purposes. Cosmetic compositions comprising calcium influx inhibitors surprisingly act to decrease melanin synthesis, and accordingly find use in skin or hair lightening products, e.g., for treating and/or preventing skin hyper-pigmentation, or bleaching hair. Calcium influx inhibitors that are capable of treating and/or preventing hyper-pigmented skin also can be referred to as "skin lighteners." When used for lightening hair, they also can be referred to "hair lighteners." Compositions used in hyper-pigmentation applications will comprise an effective amount of one or more calcium influx inhibitors to treat and/or prevent hyper-pigmentation, such as, e.g., to lighten skin/hair in an affected area.

In certain embodiments, compositions of the instant invention comprise a yeast/*C. borealis* fermentation extract, in combination with at least one calcium influx inhibitor, in an amount sufficient to decrease melanin synthesis in a given area of skin (or hair) when topically applied thereto.

In some embodiments, the cosmetic compositions for treating and/or preventing hyper-pigmentation, e.g., lightening skin (or hair), further comprise at least one other skin lightener (or at least one other hair lightener). For example, the cosmetic composition may comprise a modified peptide comprising a metal-complexed peptide comprising yeast/*C. borealis* fermentation extract, and/or a calcium influx inhibitor, in an amount effective to treat and/or prevent hyper-pigmentation may further comprise at least one other skin lightener (or at least one other hair lightener). For example, a tyrosine inhibitor, including any of the tyrosine inhibitors disclosed in KR 2005095167; JP 2003252743; and JP 61260009, may be included, in some embodiments. Any other substances that can be applied to the skin (or hair) to lighten the skin (or hair) may also be used as an additional skin (or hair) lightener with the compositions described herein. Examples of skin lighteners include, without limitation, hydroquinone, kojic acid, N-acetyl glucosamine, licorice and/or its derivatives, ascorbic acid and/or its derivatives, arbutin, bearberry extract, *Glycyrrhiza glabra* and its derivatives, *Chlorella vulgaris* extract, *perilla* extract, coconut fruit extract, and/or other depigmenting agents. *Perilla* extract is disclosed as a whitening agent, e.g., in U.S. Pat. No. 5,980,904 and Japanese Publications Nos. 07025742, 07187989, 10265322, 2001163759, and 2001181173. Coconut fruit extract is disclosed as a whitening agent in Japanese Patent No. 2896815B2.

Other skin lighteners include extracts of *Butea frondosa, Naringi crenulata, Stenoloma chusana, Azadirachta indica, Glycyrrhiza glabra linn., Morinda citrifolia*, tomato glycolipid, thiodipropionic acid (TDPA) and/or its derivatives, or any combinations thereof, as well as, ascorbyl glucoside, vitamin C, retinol and/or its derivatives, arbutin, *rumex crispus* extract, milk proteins including hydrolyzed milk proteins, N,N,S-tris(carboxymethyl)cysteamine, oleanolic acids, *perilla* oils, placenta extract, saxifragia sarmentosa, juniperic acid, thiodipropionic acid (TDPA) and/or its derivatives, *ligusticum chiangxiong hort., asmunda japonica thunb., stellaria medica* (L.) *cyr., sedum sarmentosum bunge, ligusticum lucidum Ait., ilex purpurea hassk*, emblica, apigenin, ascorbyl palmitol, carruba *C. borealis* s, hesperitin, inabata *C. borealis*, isoliquirtigenin, kaempherol-7-neohesperidose, L-mimosine, luteolin, oil-soluble licorice extract P-T (40), oxa acid, phenyl isothiocyanate, cococin, silymarin, T4CA, teterahydro curcumin, unitrienol, ursolic-oleanolic acid, UVA/URSI, or any combinations thereof. Further, it is contemplated that synergistic improvements may be obtained with combinations of one or more such additional skin (or hair) lighteners with compositions of the instant invention, in some embodiments. For example, in some embodiments, the invention relates to synergistic action of one or more compositions described herein with TDPA, e.g., to provide enhanced skin lightening benefits to skin.

Skin Thickness

In addition to the effect of DICKKOPF-1 expression enhancers on skin pigmentation, DICKKOPF-1 expression enhancers also increase skin thickness in non-palmoplantar skin. This is useful in treating a variety of dermatological conditions, for instance skin grafts, skin ulcers, skin abrasions or avulsion/excisions (such as those that leave a volume defect), injuries or predispositions to injury caused by repetitive impacts or mechanical stress, age-related skin changes (for instance, thinning or wrinkled skin), or skin damage due to steroid treatment.

The epidermis in palmoplantar areas of the skin is thicker and less pigmented than in non-palmoplantar areas. Fibroblasts in palmoplantar dermis induce a thick epidermis and keratin 9 expression in non-palmoplantar keratinocytes through mesenchymal-epithelial interactions, whereas fibroblasts in non-palmoplantar dermis do not (Yamaguchi et al., J. Invest. Dermatol. 112:483-488, 1999).

Non-palmoplantar epidermis (excluding dermal components) can be grafted to treat palmoplantar skin defects (e.g. caused by diabetes mellitus (Yamaguchi et al., Brit. J. Dermatol. 151:1019-1028, 2004) and rheumatic diseases (Yamaguchi et al., Brit. J. Dermatol. 152:664-672, 2005)) because it can adopt a palmoplantar phenotype through mesenchymal-epithelial interactions (Yamaguchi et al., Arch. Dermatol. 137:621-628, 2001; Yamaguchi and Yoshikawa, J. Dermatol. 28:521-534, 2001).

DICKKOPF-1, which interacts with the Wnt receptor lipoprotein receptor-related protein 6 (LRP6; Mao et al., Nature 411:321-325, 2001), is a secreted antagonist of the canonical Wnt signaling pathway, which involves beta-catenin and multiple protein complexes containing glycogen synthase kinase 3.beta. (GSK3.beta.), axin, adenomatous polyposis coli (APC) and Akt (Kawano & Kypta, J. Cell Sci. 116:2627-2634, 2003).

HOX gene family members are transcription factors regulating patterning in the primary and secondary axes of developing embryos which also control digit number and morphogenesis (Zakany et al., Science 304:1669-1672, 2004). The collinear regulation of HOX genes during limb development is similar to that seen in the trunk: genes located in the middle of the HoxD complex (HoxD8) are expressed in proximal areas of the limb bud whereas genes located upstream have a more distal expression (HoxD12; Kmita et al., Nature 420: 145-150, 2002). HOX genes are also known to direct topographical/site-specific differentiation of embryonic neurons in response to growth factors, especially those secreted by fibroblasts (Dasen et al., Nature 425:926-933, 2003), and DICKKOPF-1's effect on HOX gene expression—amplified by overexpression of DICKKOPF-1 mediated by administration of DICKKOPF-1 expression enhancing agents such as yeast/C. borealis fermentation extract—may result in expression of palmoplantar phenotype and/or one or more characteristics thereof.

Provided herein is an exemplary protocol for treating a subject with thin skin, for instance due to aging or treatment with topical steroids. However, one of skill in the art can see that such a treatment protocol is also suitable for the treatment of other conditions resulting in thin skin, for example when the subject has a skin graft, an ulcer, an abrasion, or an injury caused by a repetitive impact or mechanical stress. In some embodiments, the skin being treated is on the hands, for instance, in age-related thinning of the skin, and in certain examples, the DICKKOPF-1 expression enhancer is provided in the form of a hand creme or lotion.

In some embodiments, the subject has a palmoplantar burn, a foot ulcer, for instance a diabetic foot ulcer, or another type of erosion injury, such as those resulting from collagen diseases, such as systemic sclerosis, poly arthritis nodosa, and rheumatoid arthritis. These types of skin injuries are treated, in some examples, with grafts of trunk-derived epidermis or tissue engineered from fibroblasts, which is induced by DICKKOPF-1 to adopt a plantar phenotype. The plantar phenotype results in a more durable skin graft that is resistant to further damage. Thus, otherwise intractable palmoplantar wounds, for instance those with exposed bones, can be treated, for instance, with a combination of bone marrow exposure, occlusive dressing, epidermal grafting, and treatment with DICKKOPF-1. See, for instance, Atiyeh et al., (2005) Burns, 31:944-956, for a review of methods of closing burns and other wounds; Wong et al., (2007) Br. J. Dermatol. 156:1149-1155, for a review of methods of using fibroblasts for tissue engineering; and Yamaguchi et al. (2004) Br. J. Dermatol. 151:1019-1028, for methods of healing intractable diabetic foot ulcers with exposed bones, all of which are incorporated herein by reference. In each case, the graft tissue is exposed to DICKKOPF-1, either before or after transplantation, in order to induce a durable palmoplantar phenotype.

Topical DICKKOPF-1 expression enhancer therapy is suitable for treating acutely thinning skin or skin grafts, as well as for maintaining the improvement seen following treatment of the acute condition. Briefly, an emulsion-based DICKKOPF-1 expression enhancer formulation is applied topically to the affected area of the subject one, twice, or more daily, generally morning and evening. The typical dose of DICKKOPF-1 expression enhancer ranges from 0.1 .mu.g per kg of body weight to 1 .mu.g per kg of body weight, depending on the severity of the condition, the age of the subject, and the sensitivity of the subject to adverse side effects such as burning or redness. In certain examples, about 10-1,000 ng/ml DICKKOPF-1 expression enhancer is applied topically, for instance, from about 50 ng/ml to about 500 ng/ml, or about 100 ng/ml. Treatment is continued for at least six weeks or until the desired effect is achieved. In some cases, treatment is continued for 12, 24, 36 or more weeks.

Once the desired degree of skin thickening is achieved, DICKKOPF-1 expression enhancer application is reduced to once a day. In some cases, treatment will continue indefinitely, whereas in other cases treatment is discontinued after a period of maintenance treatment.

Without further elaboration, it is believed that one skilled in the art can, using this description, utilize the present discoveries to their fullest extent. The following examples are illustrative only, and not limiting of the disclosure in any way whatsoever.

EXAMPLES

Example 1

Preparation of C. borealis Extract

*Clintonia borealis* is harvested and prepared as a 1:5 aqueous infusion where 200 mg of dry plant material yields 1 ml of extract. The infusion is a solvent-free, aqueous preparation.

Example 2

Preparation of Yeast/C. borealis Fermentation Extract

*Clintonia borealis* extract as described above is fermented with standard *Pichia pastoris* fermentation media for a period of between 72-140 hours until the plant components are at least partially metabolized as assessed by measurement of optical density. The crude yeast/*Clintonia borealis* extract is lysed and ground to free water soluble cell wall components including polysaccharides. The insoluble components are removed by filtration so as to improve color and odor. The final liquid fermentation extract product is preserved.

Example 3

Tissue Culture of Fibroblasts

Human dermal fibroblast, adult (22 yrs; Cascade; #5C0759) were grown in fibroblast growth media containing 10% FBS, 1% L-Glutamine, and 1% P/S. The fibroblasts were seeded on 6-well plates at density of 350,000 cells/well and incubated overnight. Supernatants were removed from the wells. Serum free media (1% L-Glutamine, 1% P/S, and no FBS) containing either a vehicle or Yeast/C. borealis Fermentation Extract were added to the cells. Cell lysates were collected 48 hours after the treatment.

Example 4

Determination of Protein Concentration

Protein concentration was determined by Coomassie protein assay. Briefly, standards were made using bovine serum albumin (BSA). 1:100 diluted cell lysates were prepared. The standards and lysates were mixed with equal amount of Coomassie solution (#1856209; Thermo Scientific). 0.2 ml of mixture was added to 96 well-plates and read at 570 nm.

Example 5

DICKKOPF-1 Amount Determination

DICKKOPF-1 amount was determined using Human DICKKOPF-1 ELISA Kit from R&D System (DY1906E). Manufacturer's protocol was followed. Briefly, 96 well-plates were coated with 4 microG/ml of Capture Antibody at 100 microL/well overnight. The plates were washed 3× and blocked with 300 microL/well of Reagent Diluent (1% BSA in PBS) for 1 hour. The plates were washed 3×. Test samples were prepared using data from Coomassie protein assay; thus, all samples have equal amount of protein. DICKKOPF-1 standards and the test samples were added to the plates at 100 microliters/well for 2 hours. The plates were washed 3×, then 100 microliters of Detection Antibody (50 ng/ml) added and incubated for two hours. The plates were washed 3× followed by addition of 100 microliters/well of Streptavidin-HRP for 20 minutes. The plates were washed 3×, then 100 microliters/well of Substrate Solution was added for 20 minutes. 50 microliters/well of Stop Solution was added followed by gently tapping of the plates. The plates were read at 450 nm.

Example 6

In Vitro Increase in DICKKOPF-1 Expression after Treatment with *C. borealis*/Yeast Fermentation Extract As shown in Table 1, fibroblasts treated with the yeast/*C. borealis* fermentation extract induced DICKKOPF-1 expression in protein level.

TABLE 1

| Active | Conc. | % Change | P value |
| --- | --- | --- | --- |
| Yeast/*C. borealis* Fermentation Extract | 1.0000% | 38.97% | 0.002 |
| | 0.2000% | 49.30% | 0.001 |
| | 0.0400% | 13.91% | 0.047 |
| | 0.0080% | 31.68% | 0.004 |
| | 0.0016% | 54.36% | 0.000 |

Example 7

In Vitro Skin Lightening by Yeast/*C. borealis* Fermentation Extract

An experiment was designed to evaluate the ability of Yeast/*C. borealis* Fermentation Extract to demonstrate skin lightening efficacy in vitro in the presence of known skin lightening agents. Two blends of ingredients were prepared: Blend 1 contained Thiodipropionic acid/ester, tetrahexyldecyl ascorbate, stressed yeast extract, for example as described in U.S. Patent Publication Serial No. 2011/0052517 yeast extract/agouti peptide, ascorbyl glucoside, Blend 2 contained Blend 1 ingredients+yeast/*C. borealis* fermentation extract. Tyrosinase expression was used a measure of skin lightening efficacy as it is the rate limiting enzyme for melanin synthesis.

The test was performed using Melanoderm™ FTB (MEL-300-FTB; Mattek, Ashland, Mass.), a reconstituted three-dimensional human skin equivalent tissue model containing normal keratinocytes, melanocytes (derived from African-American) and fibroblasts. The tissues were grown in MEL-300-FT-NMM-113 medium as recommended by manufacturer. After 24 hours of equilibration, the tissues were treated with 100 microL of vehicle control or the blends. After 24 hours of incubation, epidermal portion of tissues were collected for mRNA analysis. Tissues were lysed, total RNA was isolated using Qiagen reagents as per manufacturer's protocol. Tyrosinase mRNA was quantified by qPCR method as per protocol and reagents provided by Applied Biosystems, Inc.

Both blends demonstrated down-regulation of Tyrosinase mRNA expression relative to vehicle control. Blend 1 showed a 32.7% inhibition relative to vehicle control. However, Blend 2 containing yeast/*C. borealis* fermentation extract showed 42.2% inhibition, which is 26% greater compared to Blend 1. This demonstrated that Yeast/*C. borealis* fermentation extract can provide skin lightening efficacy via inhibition of tyrosinase.

Example 8

In Vitro Skin Lightening by Formulation Containing Yeast/*C. borealis* Fermentation Extract The ability of a skin care formulation containing Yeast/*C. borealis* fermentation extract to inhibit melanin synthesis was evaluated using Melanoderm™ FTB (MEL-300-FTB; Mattek, Ashland, Mass.), a reconstituted three-dimensional human skin equivalent tissue model containing normal keratinocytes, melanocytes (derived from African-American) and fibroblasts. The tissues were grown in MEL-300-FT-NMM-113 medium as recommended by manufacturer. 10 microL of the Essence Formula (similar to Example 13) was applied topically on Days 1, 2, 4, 7, 9, and 11. Before each application, the tissues (n=4 or 5) were washed with 300 microL of Phosphate Buffered Saline two times. On day 14, melanin content in the tissues was determined. Briefly, the tissues were homogenized in 0.4 ml of 1% SDS, 50 mM EDTA, and 10 mM Tris, pH 6.8. To each homogenate, 20 microL of Proteinase K (5 mg/ml) was added and incubated overnight at 45° C. An additional 20 microL of Proteinase K was added and incubated for 4 hours at 45° C. Then 50 microLl of 0.5M sodium carbonate and 10 microL of 30% $H_2O_2$ were added and incubated at 80° C. for 30 minutes. The tissues were cooled down, and the mixture was extracted with 100 microLl of chloroform/methanol (2:1). After centrifugation at 10,000 g for 10 minutes, absorption of the top phase was measured at 405 nm. Images of the tissues were taken prior to the melanin isolation.

Figure 2:
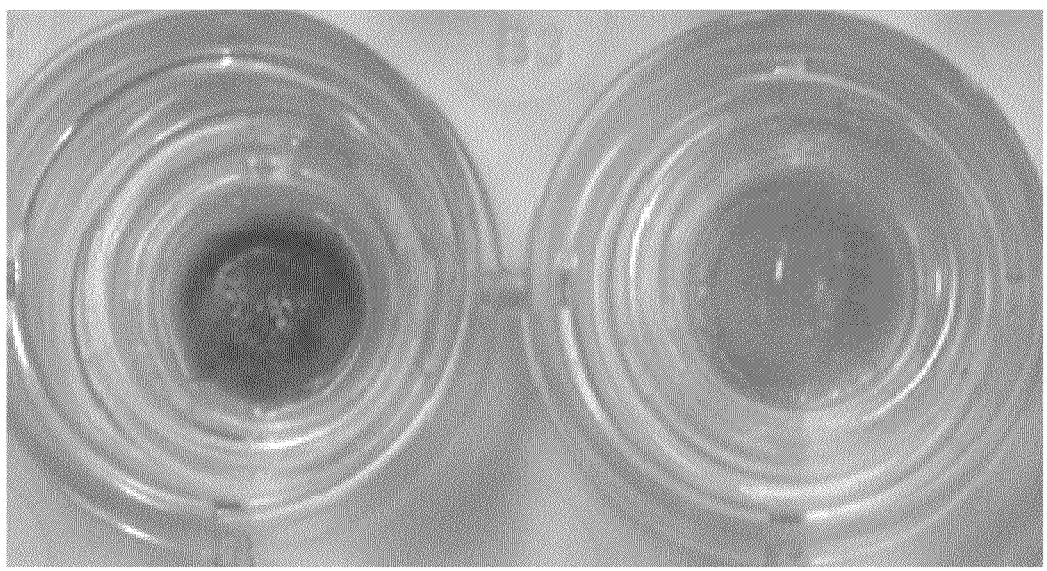
FIG. 2: Melanoderm™ 3D skin equivalent tissues where treated with a formulation of the instant invention (EX. 13) or left untreated. After 14 days, a photograph was taken to depict the visual appearance of the tissues. The treated Melanoderm™ exhibited a lighter pigmentation than the untreated Melanoderm™.

The melanin content of untreated tissues was 23.4 units whereas the melanin content of tissues treated with the skin care formulation was 12.4 units. The relative melanin content decrease in skin treated with the essence formula (Example 13) versus untreated with the essence formula is depicted in FIG. 1, while a visual depiction of the appearance of Melanoderm™ skin equivalent tissue after 14 days is shown in FIG. 2.

Example 9

Consumer Panel Test

The compositions of the instant invention may be tested on multiple subjects (panelists) and compared, for instance, to commercially available topical compositions. As will be appreciated by the practitioner, panelists can be asked to apply the control composition and a prototype to their skin over a period of hours, days, or months, and evaluate the formulations based on a questionnaire. For instance, panelists may be asked whether the prototype decreases pigmentation; lightens skin; treats hyperpigmented skin; increases skin thickness; reduces skin hirsuteness; and/or changes skin phenotype from non-palmoplantar to palmoplantar The results may demonstrate the improvement of lightening skin; treating hyperpigmented skin; decreasing pigmentation; increasing skin thickness; reducing skin hirsuteness; and/or changing skin phenotype from non-palmoplantar to palmoplantar due to an application of the prototype.

Example 10

In Vivo Evaluation of Skin Benefits Provided by a Topical Formulation Containing Yeast/*C. Borealis* Fermentation Extract A clinical efficacy study was conducted to evaluate the ability of a topical skin care Essence formulation containing Yeast/*C. borealis* fermentation extract, along with other select skin lightening ingredients, to affect attributes associated with photodamaged skin on the face. A randomized, blinded study was conducted where 34 women, in the age range of 25-40 years, were recruited to apply the product substantially described in EXAMPLE 13 twice daily on the face for twelve weeks. Photographs were taken at baseline, weeks 2, 4, 8 and 12. Photographs were evaluated by a Board-Certified dermatologist for the following skin attributes on the 0-9 scale wherein a grade of 9 corresponds to the most severe condition: discrete pigmentation, mottled pigmentation, crow's feet fine lines and wrinkling, crow's feet coarse lines and wrinkling, even skin tone, clarity and sallowness. For each of these parameters, the mean percent change from baseline at each time point was compared to the baseline values using a paired t-test. A p value of </=0.05 was considered significant. The percentage of subjects that exhibited improvement from baseline was also calculated.

TABLE 2

| | Mean % Magnitude of Improvement from Baseline [% of Panelists with Improvement from Baseline] | | | |
|---|---|---|---|---|
| Parameters | Week 2 N = 34 | Week 4 N = 34 | Week 8* N = 30 | Week 12 N = 34 |
| DISCRETE PIGMENTATION | 5 [21] | 19 [65] | 29 [80] | 32 [74] |
| MOTTLED PIGMENTATION | 11 [41] | 37 [94] | 43 [100] | 50 [97] |
| CROW'S FEET FINE LINES & WRINKLING | 15 [41] | 40 [79] | 48 [90] | 51 [94] |
| CROW'S FEET COARSE LINE & WRINKLING | Ns | 11 [18] | 39 [40] | 30 [29] |
| EVEN SKIN TONE | 12 [59] | 29 [97] | 34 [100] | 32 [97] |
| CLARITY | 17 [74] | 28 [88] | 31 [93] | 33 [97] |
| SALLOWNESS | 7 [24] | 10 [38] | 15 [53] | 18 [62] |

NS: Non-Significant mean magnitude of improvement from baseline based on a paired t-Test at p ≤ 0.05 significant level.

Example 11

Skin Thickening In Vivo

The effect of the inventive abstract on stimulating DICKKOPF-1—modulated skin thickening will be evaluated using skin equivalent 3D tissue such as Melanoderm™ FTB (MEL-300-FTB; Mattek, Ashland, Mass.). The composition containing the yeast extract of *C. borealis* will be applied either on the tissue topically or in medium basolaterally for a period of days. At the end of the treatment, tissue sections will be fixed with 4% paraformaldehyde, and Fontana-Masson staining wil be conducted. The thickness of the skin equivalent will be measured using a microscope.

Example 12

Skin Lightening and/or Anti-Aging Essence Formulation

Exemplary cosmetic compositions comprising modified yeast peptide fractions comprising yeast/*C. borealis* fermentation extract for topical application to the skin are provided below. The compositions are provided in the form of an essence that finds use in anti-aging and/or skin lightening applications.

| Description | Amount |
|---|---|
| DEMINERALIZED WATER | QS TO 100 |
| CARBOPOL 934 | 0-1 |
| ACRYLATES/C10-30 ALKYL ACRYLATE CROSSPOLYMER | 0-1 |
| ACRYLATES/C10-30 ALKYL ACRYLATE CROSSPOLYMER | 0-1 |
| XANTHAN GUM | 0-1 |
| DISODIUM EDTA-TECH.GRADE | 0-1 |
| METHYLPARABEN | 0-1 |
| ALCOHOL SD 40B | 3-5 |
| ALCOHOL MIXTURE (3210&1901 92.52-7.48) | 0-1 |
| ALCOHOL MIXTURE (3215&1901 92.52-7.48) | 0-1 |
| PHENOXYETHANOL-98% MIN (*RI*) | 0-1 |
| BUTYLENE GLYCOL | 0-3 |
| PENTYLENE GLYCOL (*RI*) | 0-4 |
| ETHOXYDIGLYCOL | 0-2 |
| ISODODECANE | 0-3 |
| SILICA SHELLS | 0-1 |
| SODIUM HYDROXIDE SOLUTION 50% | 0-3 |
| SILICONE FLUID SF-96-5 | 0-2 |
| PEG-40 STEARATE | 0-1 |
| STEARETH-2 | 0-1 |
| SOYBEAN (*GLY. SOJA*) SD.EXT./AQ/GLY./PRES. | 0-1 |
| CARROT (*DAUCUS CAROTA SATIVA*) ROOT EXTRACT/PG/AQ | 0-1 |
| PHYTOL | 0-1 |
| DIMETHICONE/DIMETH. CROSSPOLYMER | 0-2 |
| YEAST POLYSACCHARIDES (FERMENTED W/*CLINTONIA BOREALIS* EXTRACT)/AQ/PRES. | 0-2 |

Example 13

Skin Lightening and/or Anti-Aging Essence Formulation

Further exemplary cosmetic compositions comprising yeast/*C. borealis* fermentation extract for topical application to the skin are provided below. The compositions again are provided in the form of an essence that finds use in anti-aging and/or skin lightening applications, and are designated as w/w percentages of an entire exemplary cosmetic composition.

| Description | Amount |
|---|---|
| DEMINERALIZED WATER | 70-80 |
| CARBOPOL 934 | 0-1 |
| ACRYLATES/C10-30 ALKYL ACRYLATE CROSSPOLYMER | 0-1 |
| ACRYLATES/C10-30 ALKYL ACRYLATE CROSSPOLYMER | 0-1 |
| XANTHAN GUM | 0-1 |
| DISODIUM EDTA-TECH.GRADE | 0-1 |
| METHYLPARABEN | 0-1 |
| ALCOHOL SD 40B | 3-5 |
| ALCOHOL MIXTURE (3210&1901 92.52-7.48) | 0-1 |
| ALCOHOL MIXTURE (3215&1901 92.52-7.48) | 0-1 |
| PHENOXYETHANOL-98% MIN (*RI*) | 0-1 |
| BUTYLENE GLYCOL | 0-3 |
| PENTYLENE GLYCOL (*RI*) | 0-4 |
| ETHOXYDIGLYCOL | 0-2 |
| ISODODECANE | 0-3 |
| DILAURYL THIODIPROPIONATE | 0-1 |
| TETRAHEXYLDECYL ASCORBATE | 0-1 |
| ASCORBYL GLUCOSIDE (*RI*) | 0-2 |
| GLYCYRRHIZINATE-DIPOTASSIUM UNP. | 0-1 |
| SILICA SHELLS | 0-1 |
| SODIUM HYDROXIDE SOLUTION 50% | 0-3 |
| SILICONE FLUID SF-96-5 | 0-2 |
| PEG-40 STEARATE | 0-1 |
| STEARETH-2 | 0-1 |
| *SAXIFRAGA SARMENTOSA*/GRAPE EXT.BG/AQU. | 0-1 |
| *SACCHAROMYCES*/ZINC FERMENT/BG/AQ/PRES. | 0-1 |
| YEAST EXTRACT/AQ/PRES | 0-1 |
| KUDZU (*PUERARIA LOBATA*) SYMBIOSOME EXT/AQ/PRES. | 0-1 |
| SOYBEAN (*GLY. SOJA*) SD.EXT./AQ/GLY./PRES. | 0-1 |
| CARROT (*DAUCUS CAROTA SATIVA*) ROOT EXTRACT/PG/AQ | 0-1 |
| PHYTOL | 0-1 |
| DIMETHICONE/DIMETH. CROSSPOLYMER | 0-2 |
| THIODIPROPIONIC ACID | 0-2 |
| YEAST POLYSACCHARIDES (FERMENTED W/*CLINTONIA BOREALIS* EXTRACT)/AQ/PRES. | 0-5 |

Example 14

Antiperspirant/Deodorant Formulation

Exemplary cosmetic compositions comprising modified yeast peptide fractions comprising a yeast/*C. borealis* fermentation extract for topical application to the skin are provided below. The compositions are provided in the form of a deodorant that finds use in anti-aging and/or skin lightening applications.

| | |
|---|---|
| Water | qs |
| POP (15M) stearyl ether | 1-3% |
| Isopropyl Palmitate | 1-3% |
| Steareth-2 | 1-4% |
| Aluminum Chlorohydarte | up to 25% (or Aluminum zirconium trichlorohydrate up to 20%) |
| Yeast/*C. borealis* fermentation Extract | 0.001-3% |

Example 15

Toner

Exemplary cosmetic compositions comprising modified yeast peptide fractions comprising a yeast/*C. borealis* fermentation extract for topical application to the skin are provided below. The compositions are provided in the form of a toner that finds use in anti-aging and/or skin lightening applications.

Toner

| Description | Amount |
|---|---|
| DEMINERALIZED WATER | 70-80 |
| GLYCERIN | 0-10 |
| DIPROPYLENE GLYCOL | 0-10 |
| DISODIUM EDTA-TECH.GRADE | 0-1 |
| ASCORBYL GLUCOSIDE (*RI*) | 0-10 |
| THIODIPROPIONIC ACID | 0-10 |
| SODIUM HYDROXIDE SOLUTION 50% | 0-10 |
| POTASSIUM PHOSPHATE DIBASIC | 0-1 |
| SODIUM PHOSPHATE MONOBASIC ANHYD | 0-1 |
| GLYCYRRHIZINATE-DIPOTASSIUM UNP. | 0-1 |
| YEAST EXTRACT/AQ/PRES | 0-1 |
| SOYBEAN (*GLY. SOJA*) SD.EXT./AQ/GLY./PRES. | 0-1 |
| KUDZU (*PUERARIA LOBATA*) SYMBIOSOME EXT/AQ/PRES. | 0-0.1 |
| POLYQUATERNIUM-51/AQ. | 0-1 |
| CARROT (*DAUCUS CAROTA SATIVA*) ROOT EXTRACT/PG/AQ | 0-0.5 |
| *SACCHAROMYCES*/ZINC FERMENT/BG/AQ/PRES. | 0-0.5 |
| YEAST POLYSACCHARIDES (FERMENTED W/*CLINTONIA BOREALIS* EXTRACT)/AQ/PRES. | 0-2 |
| POE (20M) SORBITAN MONOLAURATE | 0-1 |
| POE (20M) SORBITAN MONOOLEATE | 0-1 |
| C12-15 ALCOHOLS BENZOATE | 0-1 |
| TETRAHEXYLDECYL ASCORBATE | 0-1 |
| PHYTOL | 0-1 |
| ALGAE (*PHAEODACTYLUM TRICORNUTUM*) EXTRACT/CAPRYLIC CAPRIC TRIGLYC./TOC. | 0-1 |
| GAMMA ORYZANOL | 0-1 |
| FRAGRANCE | 0-1 |
| ALCOHOL SD 40B | 0-10 |
| ETHOXYDIGLYCOL | 0-10 |
| PHENOXYETHANOL-98% MIN (*RI*) | 0-5 |
| METHYLPARABEN | 0-5 |
| DIAZOLIDINYL UREA-100% | 0-5 |

Example 16

Day Cream

Exemplary cosmetic compositions comprising modified yeast peptide fractions comprising a yeast/*C. borealis* fermentation extract for topical application to the skin are provided below. The compositions are provided in the form of a day cream that finds use in anti-aging and/or skin lightening applications.

Day Cream

| Description | Amount |
| --- | --- |
| DEMINERALIZED WATER | 60-80 |
| BUTYLENE GLYCOL | 0-10 |
| DISODIUM EDTA-TECH.GRADE | 0-1 |
| CARBOPOL 940 | 0-1 |
| XANTHAN GUM | 0-1 |
| SODIUM HYDROXIDE SOLUTION 50% | 0-1 |
| DIMETHYL POLYSILOXANE BLEND 12/88 | 0-10 |
| ACRYLATES/C10-30 ALKYL ACRYLATE CROSSPOLYMER | 0-1 |
| ISONONYL/ISONONANOATE | 0-10 |
| ETHYLHEXYL-METHOXYCINNAMATE | 0-10 |
| BENZOPHENONE-3 (OXYBENZONE) | 0-10 |
| OCTYL SALICYLATE | 0-10 |
| BUTYL METHOXYDIBENZOYLMETHANE | 0-10 |
| CETEARYL GLUCOSIDE | 0-10 |
| CETEARYL ALCOHOL/CETEARETH-20 | 0-10 |
| POE (24M) CHOLESTEROL ETHER | 0-1 |
| *KAEMPFERIA GALANGA* ROOT EXTRACT-100% | 0-1 |
| DILAURYL THIODIPROPIONATE | 0-10 |
| CYCLOMETHICONE-PENTAMER | 0-10 |
| *SAXIFRAGA SARMENTOSA*/GRAPE EXT.BG/AQU. | 0-5 |
| SILICA-SPHERICAL-2 TO 20 MICRONS | 0-10 |
| SOYBEAN (*GLY. SOJA*) SD.EXT./AQ/GLY./PRES. | 0-1 |
| POLYMETHYLSILSESQUIOXANE | 0-10 |
| *SACCHAROMYCES*/ZINC FERMENT/BG/AQ/PRES. | 0-1 |
| YEAST EXTRACT/AQ/PRES | 0-1 |
| YEAST POLYSACCHARIDES (FERMENTED W/ *CLINTONIA BOREALIS* EXTRACT)/AQ/PRES. | 0-2 |
| PHYTOL | 0-1 |
| TETRAHEXYLDECYL ASCORBATE | 0-1 |
| ASCORBYL GLUCOSIDE (*RI*) | 0-1 |
| CAPRYLYL GLYCOL/PHENOXYETHANOL/HEXYLENE GLYCOL-BL. | 0-10 |
| KUDZU (*PUERARIA LOBATA*) SYMBIOSOME EXT/AQ/PRES. | |
| CARROT (*DAUCUS CAROTA SATIVA*) ROOT EXTRACT/PG/AQ | 0-1 |
| FRAGRANCE | 0-5 |

Example 17

Milky Lotion

Exemplary cosmetic compositions comprising modified yeast peptide fractions comprising a yeast/*C. borealis* fermentation extract for topical application to the skin are provided below. The compositions are provided in the form of a milky lotion that finds use in anti-aging and/or skin lightening applications.

Milky Lotion

| Description | Amount |
| --- | --- |
| DEMINERALIZED WATER | 60-80 |
| CARBOPOL 940 | 0-1 |
| ACRYLATES/C10-30 ALKYL ACRYLATE CROSSPOLYMER | 0-1 |
| GLYCERIN | 0-10 |
| DISODIUM EDTA-TECH.GRADE | 0-1 |
| ETHOXYDIGLYCOL | 0-10 |
| PEG-40 STEARATE | 0-5 |
| STEARETH-2 | 0-5 |
| DILAURYL THIODIPROPIONATE | 0-10 |
| PENTAERYTHRITOL TETRAOCTANOATE | 0-10 |
| POE (20M) METHYL GLUCOSE ETHER | 0-5 |
| GAMMA ORYZANOL | 0-1 |
| PHYTOL | 0-1 |
| TETRAHEXYLDECYL ASCORBATE | 0-10 |
| DIMETHICONE/DIMETH. CROSSPOLYMER | 0-10 |
| DIMETHICONE/DIMETHICONOL 87/13% | 0-10 |
| ISOHEXADECANE | 0-10 |
| PHENOXYETHANOL-98% MIN (*RI*) | 0-5 |
| ALGAE (*PHAEODACTYLUM TRICORNUTUM*) EXTRACT/CAPRYLIC CAPRIC TRIGLYC./TOC. | 0-1 |
| ASCORBYL GLUCOSIDE (*RI*) | 0-10 |
| SODIUM HYDROXIDE SOLUTION 50% | 0-5 |
| *SAXIFRAGA SARMENTOSA*/GRAPE EXT.BG/AQU. | 0-1 |
| IMIDAZOLIDINYL UREA | 0-5 |
| *SACCHAROMYCES*/ZINC FERMENT/BG/AQ/PRES. | 0-1 |
| YEAST EXTRACT/AQ/PRES | 0-1 |
| KUDZU (*PUERARIA LOBATA*) SYMBIOSOME EXT/AQ/PRES. | 0-1 |
| SOYBEAN (*GLY. SOJA*) SD.EXT./AQ/GLY./PRES. | 0-1 |
| CARROT (*DAUCUS CAROTA SATIVA*) ROOT EXTRACT/PG/AQ | 0-1 |
| YEAST POLYSACCHARIDES (FERMENTED W/ *CLINTONIA BOREALIS* EXTRACT)/AQ/PRES. | 0-2 |
| SILICA-SPHERICAL-2 TO 20 MICRONS | 0-10 |
| BUTYLENE GLYCOL | 0-10 |
| PENTYLENE GLYCOL (*RI*) | 0-10 |
| POLYMETHYL METHACRYLATE-SPHERICAL | 0-10 |
| SILICA SHELLS | 0-5 |
| FRAGRANCE | 0-5 |

Example 18

Night Cream

Exemplary cosmetic compositions comprising modified yeast peptide fractions comprising a yeast/*C. borealis* fermentation extract for topical application to the skin are provided below. The compositions are provided in the form of a night cream that finds use in anti-aging and/or skin lightening applications.

Night Cream

| Description | Amount |
| --- | --- |
| DEMINERALIZED WATER | 60-80 |
| DISODIUM EDTA-TECH.GRADE | 0-1 |
| GLYCERIN | 0-20 |
| BUTYLENE GLYCOL | 0-10 |
| PENTYLENE GLYCOL (*RI*) | 0-10 |
| CARBOPOL 940 | 0-5 |
| ACRYLATES/C10-30 ALKYL ACRYLATE CROSSPOLYMER | 0-1 |
| SODIUM HYALURONATE-100%-JAPAN | 0-1 |
| METHYLPARABEN | 0-1 |
| CETYL CAPRYLATE | 0-10 |
| GLYCERYL TRIOCTANOATE | 0-10 |
| BEESWAX-BLEACHED | 0-5 |
| BEHENYL ALCOHOL | 0-5 |
| CETYL/STEARYL ALCOHOL (60/40) | 0-5 |
| SOYA LECITHIN/CHOLESTEROL BLEND | 0-5 |
| LECITHIN HYDROGENATED | 0-5 |
| DILAURYL THIODIPROPIONATE | 0-10 |
| GAMMA ORYZANOL | 0-1 |
| LICORICE EXTRACT PT-40-JAPAN | 0-1 |
| PHYTOL | 0-1 |
| SODIUM HYDROXIDE SOLUTION 50% | 0-5 |
| SILICONE FLUID SF-96-5 | 0-10 |
| DIMETHYL POLYSILOXANE BLEND 12/88 | 0-10 |
| HYDROXYETHYL ACRYLATE/SOD ACRYLOYLDIMETHYL COPOLYMER TAURATE/ISOHEXADECANE/POLYSORBATE 60/AQ-BL | 0-10 |
| ASCORBYL GLUCOSIDE (*RI*) | 0-1 |
| POLYQUATERNIUM-51/AQ. | 0-1 |
| CARROT (*DAUCUS CAROTA SATIVA*) ROOT EXTRACT/PG/AQ | 0-1 |

-continued

| Description | Amount |
|---|---|
| SOYBEAN (*GLY. SOJA*) SD.EXT./AQ/GLY./PRES. | 0-1 |
| GLYCYRRHIZINATE-DIPOTASSIUM UNP. | 0-1 |
| *SACCHAROMYCES*/ZINC FERMENT/BG/AQ/PRES. | 0-1 |
| *SAXIFRAGA SARMENTOSA*/GRAPE EXT.BG/AQU. | 0-1 |
| YEAST EXTRACT/AQ/PRES | 0-1 |
| KUDZU (*PUERARIA LOBATA*) SYMBIOSOME EXT/AQ/PRES. | 0-1 |
| YEAST POLYSACCHARIDES (FERMENTED W/*CLINTONIA BOREALIS* EXTRACT)/AQ/PRES. | 0-2 |
| TETRAHEXYLDECYL ASCORBATE | 0-1 |
| ALGAE (*PHAEODACTYLUM TRICORNUTUM*) EXTRACT/CAPRYLIC CAPRIC TRIGLYC./TOC. | 0-1 |
| PHENOXYETHANOL-98% MIN (*RI*) | 0-5 |
| FRAGRANCE | 0-5 |

Example 19

Block SPF50

Exemplary cosmetic compositions comprising modified yeast peptide fractions comprising a yeast/*C. borealis* fermentation extract for topical application to the skin are provided below. The compositions are provided in the form of a block SPF50 that finds use in anti-aging and/or skin lightening applications.

| Description | Amount |
|---|---|
| DEMINERALIZED WATER | 20-100 |
| BUTYLENE GLYCOL | 0-10 |
| CYCLOMETHICONE-PENTAMER | 0-30 |
| PHENYL TRIMETHICONE | 0-20 |
| TRIMETHYLSILOXYSILICATE/CYCLOPENTASIL. BL | 0-10 |
| CYCLOMETH/DIMETH.COPOLYOL-92/8 | 0-10 |
| POLYGLYCERYL-3 DIISOSTEARATE-LOW ODOR | 0-1 |
| CETYL DIMETHICONE COPOLYOL | 0-1 |
| POLYMETHYL METHACRYLATE-SPHERICAL | 0-10 |
| SILICA-FUMED | 0-5 |
| LITHIUM MAGNESIUM SILICATE | 0-5 |
| ZINC OXIDE/CYCLOPENTA./DIMETH.COPOLY./METH.-USP (*RI*) | 0-60 |
| TIT.DIOX.-CYCLOPENTA./DIM.COP./AL./METH.DISP. | 0-30 |
| ETHYLHEXYL-METHOXYCINNAMATE | 0-30 |
| OCTYL SALICYLATE | 0-10 |
| GAMMA ORYZANOL | 0-1 |
| TOCOPHERYL ACETATE-SYN | 0-1 |
| ASCORBYL GLUCOSIDE (*RI*) | 0-1 |
| YEAST EXTRACT/AQ/PRES | 0-1 |
| *SACCHAROMYCES*/ZINC FERMENT/BG/AQ/PRES. | 0-1 |
| *SAXIFRAGA SARMENTOSA*/GRAPE EXT.BG/AQU. | 0-1 |
| DILAURYL THIODIPROPIONATE | 0-1 |
| SOYBEAN (*GLY. SOJA*) SD.EXT./AQ/GLY./PRES. | 0-1 |
| *PERILLA* LEAF (SHISO) AQ/ALC.EXT.-PRESERVED | 0-1 |
| CARROT (*DAUCUS CAROTA SATIVA*) ROOT EXTRACT/PG/AQ | 0-1 |
| KUDZU (*PUERARIA LOBATA*) SYMBIOSOME EXT/AQ/PRES. | 0-1 |
| MAGNESIUM SULFATE-HEPTAHYDRATE | 0-5 |
| DISODIUM EDTA-TECH.GRADE | 0-1 |
| PHENOXYETHANOL-98% MIN (*RI*) | 0-5 |
| IMIDAZOLIDINYL UREA | 0-5 |
| ALGAE (*PHAEODACTYLUM TRICORNUTUM*) EXTRACT/CAPRYLIC CAPRIC TRIGLYC./TOC. | 0-1 |
| PHYTOL | 0-1 |
| YEAST POLYSACCHARIDES (FERMENTED W/ *CLINTONIA BOREALIS* EXTRACT)/AQ/PRES. | 0-2 |
| SODIUM HYDROXIDE SOLUTION 50% | 0-1 |
| TETRAHEXYLDECYL ASCORBATE | 0-1 |

Example 20

Cleanser

Exemplary cosmetic compositions comprising modified yeast peptide fractions comprising a yeast/*C. borealis* fermentation extract for topical application to the skin are provided below. The compositions are provided in the form of a deodorant that finds use in cleanser applications.

Cleanser

| Description | Amount |
|---|---|
| DEMINERALIZED WATER | 0-50 |
| POTASSIUM HYDROXIDE 45% | 0-30 |
| GLYCERIN | 0-30 |
| BUTYLENE GLYCOL | 0-30 |
| STEARIC ACID | 0-30 |
| MYRISTIC ACID | 0-20 |
| LAURIC ACID | 0-30 |
| ETHYLENE GLYCOL DISTEARATE-JAPAN | 0-10 |
| METHYLPARABEN | 0-5 |
| POE (9M) 400 MONOLAURATE | 0-5 |
| GLYCERYL STEARATE/PEG-100 STEARATE | 0-10 |
| POE (20M) SORBITAN MONOSTEARATE | 0-10 |
| LAURYL BETAINE-29%-JAPAN | 0-10 |
| LAUROYL SARCOSINE | 0-10 |
| DISODIUM EDTA-TECH.GRADE | 0-1 |
| HYDROXYETHYL CELLULOSE | 0-1 |
| PHENOXYETHANOL-98% MIN (*RI*) | 0-10 |
| YEAST EXTRACT/AQ/PRES | 0-1 |
| *SACCHAROMYCES*/ZINC FERMENT/BG/AQ/PRES. | 0-1 |
| SOYBEAN (*GLY. SOJA*) SD.EXT./AQ/GLY./PRES. | 0-1 |
| YEAST POLYSACCHARIDES (FERMENTED W/*CLINTONIA BOREALIS* EXTRACT)/AQ/PRES. | 0-2 |
| TETRAHEXYLDECYL ASCORBATE | 0-1 |
| DILAURYL THIODIPROPIONATE | 0-1 |
| PHYTOL | 0-1 |
| FRAGRANCE | 0-5 |

Example 21

21 Mask

Exemplary cosmetic compositions comprising modified yeast peptide fractions comprising a yeast/*C. borealis* fermentation extract for topical application to the skin are provided below. The compositions are provided in the form of a deodorant that finds use in a mask application.

21 Mask

| Description | Amount |
|---|---|
| DEMINERALIZED WATER | 60-90 |
| SODIUM POLYACRYLATE-100% | 0-5 |
| CARRAGEENAN/GELCARIN GP 359 | 0-5 |
| DISODIUM EDTA-TECH.GRADE | 0-5 |
| METHYLPARABEN | 0-5 |
| BUTYLENE GLYCOL | 0-20 |
| PROPYLENE GLYCOL | 0-10 |
| ASCORBYL GLUCOSIDE (*RI*) | 0-1 |
| SODIUM HYDROXIDE SOLUTION 50% | 0-2 |
| POE (20M) SORBITAN MONOOLEATE | 0-10 |
| POE (20M) SORBITAN MONOLAURATE | 0-5 |
| LICORICE EXTRACT PT-40-JAPAN | 0-1 |
| ALCOHOL SD 40B | 0-10 |
| ETHOXYDIGLYCOL | 0-10 |
| PHENOXYETHANOL-98% MIN (*RI*) | 0-10 |
| SODIUM HYALURONATE-100%-JAPAN | 0-1 |
| GLYCYRRHIZINATE-DIPOTASSIUM UNP. | 0-1 |
| TETRAHEXYLDECYL ASCORBATE | 0-1 |
| YEAST EXTRACT/AQ/PRES | 0-1 |

-continued

| Description | Amount |
| --- | --- |
| THIODIPROPIONIC ACID | 0-1 |
| FRAGRANCE | 0-1 |
| SACCHAROMYCES/ZINC FERMENT/BG/AQ/PRES. | 0-1 |
| SOYBEAN (GLY. SOJA) SD.EXT./AQ/GLY./PRES. | 0-1 |
| KUDZU (PUERARIA LOBATA) SYMBIOSOME EXT/AQ/PRES. | 0-1 |
| CARROT (DAUCUS CAROTA SATIVA) ROOT EXTRACT/PG/AQ | 0-1 |
| YEAST POLYSACCHARIDES (FERMENTED W/CLINTONIA BOREALIS EXTRACT)/AQ/PRES. | 0-2 |

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description, Examples, and figures. Such modifications are also intended to fall within the scope of the appended claims. All publications cited herein are incorporated by reference in their entirety.

What is claimed is:

1. A method for treating fine lines and/or wrinkles, comprising topically applying to an area of skin in need thereof an effective amount of a composition comprising an effective amount of a DICKKOPF-1 expression increasing agent in a cosmetically acceptable vehicle, wherein said DICKKOPF-1 expression increasing agent comprises an extract of the yeast *Pichia pastoris* which, before being extracted, has been fermented in the presence of a *Clintonia borealis* extract.

2. The method of claim 1, with the proviso that the DICK-KOPF-1 expression increasing agent excludes unmetabolized *C. borealis* extract.

3. The method according to claim 1, wherein said DICK-KOPF-1 expression increasing agent is present in the composition at between about 0.0001% by weight and about 10% by weight.

4. The method according to claim 1, wherein the extract of the yeast exhibits a pH of between about 5.0 to about 7.0 when added to the composition.

5. The method according to claim 1, wherein the *C. borealis* extract is an aqueous *C. borealis* extract.

6. The method according to claim 1, wherein said composition further comprises at least one skin lightener, selected from thiodipropionic acid (TDPA) or an ester derivative thereof.

7. A method for improving skin thickness, plumpness, and/or tautness, comprising topically applying to an area of skin in need thereof an effective amount of a composition comprising an effective amount of a DICKKOPF-1 expression increasing agent in a cosmetically acceptable vehicle, wherein said DICKKOPF-1 expression increasing agent comprises an extract of the yeast *Pichia pastoris* which, before being extracted, has been fermented in the presence of a *Clintonia borealis* extract.

8. The method according to claim 1, wherein said DICK-KOPF-I expression increasing agent is applied to skin exhibiting a non-palmoplantar phenotype.

9. The method of claim 1, wherein the extract of the yeast includes cytolasmic and extracellular components extracted from the yeast fermented in the presence of the *C. borealis* extract.

10. The method of claim 7, wherein the extract of the yeast includes cytolasmic and extracellular components extracted from the yeast fermented in the presence of the *C. borealis* extract.

* * * * *